(12) United States Patent
Von Rosenberg

(10) Patent No.: US 6,753,966 B2
(45) Date of Patent: Jun. 22, 2004

(54) OPTICAL PROBES AND METHODS FOR SPECTRAL ANALYSIS

(75) Inventor: Charles W. Von Rosenberg, Belmont, MA (US)

(73) Assignee: Textron Systems Corporation, Wilmington, MA (US)

(*) Notice: Subject to any disclaimer, the term of this patent is extended or adjusted under 35 U.S.C. 154(b) by 414 days.

(21) Appl. No.: 09/803,131

(22) Filed: Mar. 9, 2001

(65) Prior Publication Data

US 2002/0039186 A1 Apr. 4, 2002

Related U.S. Application Data

(60) Provisional application No. 60/188,541, filed on Mar. 10, 2000.

(51) Int. Cl.[7] .............................................. G01N 21/00
(52) U.S. Cl. ..................................................... 356/432
(58) Field of Search .......................... 235/435; 356/402, 356/417, 73, 336, 338, 432, 433, 436; 385/12

(56) References Cited

U.S. PATENT DOCUMENTS

| | | | |
|---|---|---|---|
| 3,281,597 A | 10/1966 | Greenberg | 250/43.5 |
| 3,773,424 A | 11/1973 | Selgin | 356/181 |
| 4,003,660 A | 1/1977 | Christie, Jr. et al. | 356/178 |
| 4,260,262 A | 4/1981 | Webster | 356/418 |
| 4,260,263 A | 4/1981 | Kummer | 356/448 |
| 4,266,878 A | 5/1981 | Auer | 356/419 |
| 4,286,327 A | 8/1981 | Rosenthal et al. | 364/498 |
| 4,403,191 A | 9/1983 | Satake | 324/452 |

(List continued on next page.)

FOREIGN PATENT DOCUMENTS

| | | |
|---|---|---|
| DE | 2938844 | 4/1981 |
| DE | 3401475 A1 | 7/1985 |
| EP | 0 491 131 A1 | 6/1992 |
| EP | 0 806 653 | 5/1997 |
| GB | 2 084 723 A | 4/1982 |
| JP | 6138043 | 5/1994 |
| JP | 11-83627 A | 3/1999 |
| WO | WO 96/08710 | 3/1996 |
| WO | WO 98/11410 | 3/1998 |
| WO | WO 99/40419 | 8/1999 |

OTHER PUBLICATIONS

Partial International Search Report Mailed on Sep. 28, 2001.
International Search Report Completed on Mar. 14, 2002 and Mailed on Mar. 26, 2002.
Derwent abstract of SU 514111A, Acc. No. 1977–A3525Y, " Model Radial Axial Hydraulic Turbine Installation with Test Probe Holder at Lower Blade Ring", Patent–assignee: Lengd Metal WKS.
Baird et al.; "Compact, Self–Contained Optical Spectrometer", Appl. Spec. v.49 (11): 1, (1997).

(List continued on next page.)

Primary Examiner—Michael G. Lee
Assistant Examiner—Jamara A. Franklin
(74) Attorney, Agent, or Firm—Foley Hoag LLP

(57) ABSTRACT

The present invention relates to spectral analysis systems and methods for determining physical and chemical properties of a sample by measuring the optical characteristics of light emitted from the sample. In one embodiment, a probe head for use with a spectrometer includes a reflector for illuminating a sample volume disposed circumferentially about the light source of the probe head. In another embodiment, a probe head includes an optical blocking element for forcing the optical path between the light source and an optical pick-up optically connected to the spectrometer into the sample. The probe head also includes a reference shutter for selectively blocking light emitted from the sample from reaching the optical pick-up to facilitate calibration of the spectrometer.

25 Claims, 10 Drawing Sheets

U.S. PATENT DOCUMENTS

| | | | |
|---|---|---|---|
| 4,441,979 A | 4/1984 | Dailey | 204/402 |
| 4,540,286 A | 9/1985 | Satake et al. | 356/445 |
| 4,627,008 A | 12/1986 | Rosenthal | 364/550 |
| 4,658,147 A | 4/1987 | Eldering | 356/328 |
| 4,692,620 A | 9/1987 | Rosenthal | 250/343 |
| 4,729,247 A | 3/1988 | Brown | |
| 4,752,689 A | 6/1988 | Satake | 250/339 |
| 4,806,764 A | 2/1989 | Satake | 250/339 |
| 4,968,143 A | 11/1990 | Weston | 356/328 |
| 4,997,280 A | 3/1991 | Norris | 356/308 |
| 5,013,150 A * | 5/1991 | Watts et al. | 356/73 |
| 5,021,662 A | 6/1991 | Johnson | 250/343 |
| 5,077,481 A * | 12/1991 | Hoult | 250/576 |
| 5,092,819 A | 3/1992 | Schroeder et al. | 460/7 |
| 5,106,339 A | 4/1992 | Braun et al. | 460/7 |
| 5,128,882 A | 7/1992 | Cooper et al. | 364/550 |
| 5,148,288 A | 9/1992 | Hannah | 358/298 |
| 5,155,628 A | 10/1992 | Dosmann | 359/640 |
| 5,159,199 A | 10/1992 | LaBaw | 250/339 |
| 5,166,755 A | 11/1992 | Gat | 356/419 |
| 5,179,025 A | 1/1993 | Koontz et al. | 436/52 |
| 5,205,293 A | 4/1993 | Ito | 128/691 |
| 5,206,699 A | 4/1993 | Stewart et al. | 356/30 |
| 5,218,207 A | 6/1993 | Rosenthal | 250/341 |
| 5,241,178 A | 8/1993 | Shields | 250/339 |
| 5,258,825 A | 11/1993 | Reed et al. | 356/402 |
| 5,260,584 A | 11/1993 | Popson et al. | 250/571 |
| 5,272,518 A | 12/1993 | Vincent | 356/405 |
| 5,319,200 A | 6/1994 | Rosenthal et al. | 250/341 |
| 5,327,708 A | 7/1994 | Gerrish | 56/1 |
| 5,335,067 A | 8/1994 | Prather et al. | |
| 5,351,117 A | 9/1994 | Stewart et al. | 356/30 |
| 5,377,000 A | 12/1994 | Berends | 356/73 |
| 5,383,452 A | 1/1995 | Buchert | 128/633 |
| 5,406,084 A | 4/1995 | Tobler et al. | 250/339.01 |
| 5,418,615 A * | 5/1995 | Doyle | 356/436 |
| 5,433,197 A | 7/1995 | Stark | 128/633 |
| 5,459,313 A | 10/1995 | Schrader et al. | 250/223 B |
| 5,460,177 A | 10/1995 | Purdy et al. | 128/633 |
| 5,461,229 A | 10/1995 | Sauter et al. | 250/253 |
| 5,464,981 A | 11/1995 | Squyres et al. | 250/341.8 |
| 5,475,201 A | 12/1995 | Pike | 219/497 |
| 5,476,108 A | 12/1995 | Dominguez et al. | 131/108 |
| 5,480,354 A | 1/1996 | Sadjadi | 460/7 |
| 5,489,980 A | 2/1996 | Anthony | 356/308 |
| 5,502,799 A | 3/1996 | Tsuji et al. | 395/131 |
| 5,503,006 A | 4/1996 | Babaian-Kibala et al. | 73/86 |
| 5,510,619 A | 4/1996 | Zachmann et al. | 250/339.08 |
| 5,548,115 A | 8/1996 | Ballard et al. | 250/253 |
| 5,616,851 A | 4/1997 | McMahon et al. | 73/29.01 |
| 5,625,459 A | 4/1997 | Driver | 356/446 |
| 5,642,498 A | 6/1997 | Kutner | 395/509 |
| 5,652,810 A * | 7/1997 | Tipton et al. | 385/12 |
| 5,654,496 A | 8/1997 | Thompson | 73/1.01 |
| 5,676,143 A | 10/1997 | Simonsen et al. | 128/633 |
| 5,684,582 A | 11/1997 | Eastman et al. | 356/328 |
| 5,736,410 A | 4/1998 | Zarling et al. | 436/172 |
| 5,739,536 A | 4/1998 | Bucholtz et al. | 250/341.2 |
| 5,745,234 A | 4/1998 | Snail et al. | 356/236 |
| 5,751,421 A | 5/1998 | Wright et al. | 356/328 |
| 5,784,158 A | 7/1998 | Stanco et al. | 356/326 |
| 5,808,305 A | 9/1998 | Leidecker et al. | 250/341.98 |
| 5,813,987 A | 9/1998 | Modell et al. | 600/473 |
| 5,824,567 A | 10/1998 | Shih et al. | 438/73 |
| 5,847,825 A | 12/1998 | Alexander | 356/318 |
| 5,867,265 A | 2/1999 | Thomas | 356/328 |
| 5,872,655 A | 2/1999 | Seddon et al. | 359/588 |
| 5,880,826 A | 3/1999 | Jung et al. | 326/73 |
| 5,884,775 A | 3/1999 | Campbell | 209/581 |
| 5,953,119 A | 9/1999 | Zigler et al. | 356/326 |
| 5,957,773 A | 9/1999 | Olmsted et al. | 460/7 |
| 6,100,526 A | 8/2000 | Mayes | 250/339.11 |

OTHER PUBLICATIONS

Department of Biosystems and Agricultural Engineering, University of Minesota, 1995 Annual Report Research.

Ciurczak; Emil W. "Uses of Near–Infrared Spectroscopy in Pharmaceutical Analysis", Applied Spectroscopy Reviews 23( 1 & 2), 147–163 (1987).

Geladi et al.; " Linearization and Scatter–Correction for Near–Infrared Reflectance Spectra of Meat", Applied Spectroscopy, 39(3): 491–500, (1985).

Goddu et al.; " Spectra– Structure Correlations for the Near–Infrared Region", Analytical Chemistry, 32(1): 140–142, ( Jan. 1960).

Honigs et al.; " Near–Infrared Reflectance Analysis by Gauss–Jordan Linear Algebra", Applied Spectroscopy, 37(6): 491–497, (1983).

Honigs et al.; " A New Method for Obtaining Individual Component Spectra from Those of Complex Mixtures", Applied Spectroscopy, 38(3): 317–322, (1984).

Josefson et al.; " Optical Fiber Spectrometry in Turbid Solutions by Multivariate Calibration Applied to Tablet Dissolution Testing", Anal. Chem. 60: 2666–2671, (1988).

Keefe P. D.; "A Dedicated Wheat Grain Image Analyser", Plant Varieties and Seeds, 5:27–33, (1992).

Kisner and Brown, " Multiple Analytical Frequencies and Standard for the Least–Squares Spectrometric Analysis of Serum–Lipids", Anal. Chem. 55:1703–1707, (1983).

Lutton Christine.; " Cyberfarm", Forbes, Jul. 15, 1996.

Mosen et al.; " Determination of Impurities in Helium by Gas Chromatography", Analytical Chemistry, 32(1): 141–142, (1960).

Nyden et al.; " Spectroscopic Quantitative Analysis of Strongly Interacting Systems: Human Plasma Protein Mixtures", Applied Spectroscopy ,42 (4): 588–594, (1988).

Norris et al.; " Predicting Forage Quality Infrared Reflectance Spectroscopy", Journal of the Animal Science 43 (4): 889–897, (1976).

Osborne and Fearn; " Discriminant Analysis of Black Tea by Near Infrared Reflectance Spectroscopy", Food Chemistry 29 (1), 233–238, (1988).

Schneider et al.; " Fiber–Optic Near Infrared Reflectance Sensor For Detection of Organics in Soils", IEEE Photonics Technology Letters 7(1): 87–89, (1995).

Stark and Luchter; " Near Infrared Analysis (NIRA): A Technology for Quantitative and Qualitative Analysis", Applied Spectroscopy Reviews 22(4): 335–399, (1986).

Starr et al.; " Applications of Near Infrared Reflectance Analysis in Breeding Wheats for Bread–making Quality", Near Infrared Analysis– Today and Tomorrow?, Anal. Proc., 20: 72–74, (Feb. 1983).

Watson, C.A.; " Near Inflared Reflectance Spectrophotometric Analysis of Agricultural Products", Analytical Chemistry 49(9) : 835A–839, (Aug. 1977).

Wetzel L. David; " Near –Infrared Reflectance Analysis: Sleeper Among Spectroscopic Techniques", Analytical Chemistry 55(12): 1165A–1175A, (Oct. 1983).

Winch and Major; " Predicting Nitrogen and Digestibility of Forage Using Near Infrared Reflectance Photometry", Can. J. Plant Sci. 61:45–51, (Jan. 1981).

Better Crops With Plant Food(Journal), vol. 81 No. 4, (1997).

Yamamoto et al.; "Detection of Metals in the Environment Using a Portable Laser–Induced Breakdown Spectroscopy Instrument", Appl. Spec. V. 50(2) Abstract Only, (1997).

Rhea Corporation; "Supliers of Krestrel™ brand Systems for Imaging Spectroscopy", Rhea Corporation Information Sheet Sep. 22, 1997.

Perstorp Analytical Information Sheet, www.i–way.net.uk/sinar/product.

Fundamentals Near Infrared Instrumentation, Infrared Detectors infromation sheet.

* cited by examiner

OPTICAL PROBES AND METHODS FOR SPECTRAL ANALYSIS

REFERENCE TO RELATED APPLICATIONS

This application claims priority to U.S. Provisional Patent Application No. 60/188,541, filed Mar. 10, 2000, incorporated herein by reference.

BACKGROUND OF THE INVENTION

Most analytical techniques used in industry require taking samples to the laboratory to be analyzed by time consuming procedures. For use in the field, e.g., on-site analysis, spectral analyzers have been gaining favor because of the potential speed of analysis and the fact that they often represent a non-destructive means of analyzing samples. Based on spectroscopy technology, it is possible not only to determine the characteristics of a sample surface, but often the constituent components beneath a sample surface.

Typically, in spectroscopic applications an optimal range of wavelengths is selected to irradiate a sample, where reflected or transmitted light is measured to determine the characteristics of the sample. Some samples, for example, are best analyzed using a near infrared spectrum of light while others are optimally analyzed using a range such as visible or mid infrared spectrum.

Many spectral analyzers utilize a narrow spot size to intensely irradiate a sample to be analyzed. Illuminating a sample with a highly intense incident light typically results in an easier collection of larger amounts of reflected light, thus improving system performance. Unfortunately, a narrow spot size can sometimes provide inaccurate measurements because a small spot may not be representative of the intended sample, particularly where the sample is heterogenous in nature, such as, for example, grains, seeds, powders or and other particulate or suspended analytes. A narrow spot may unduly heat the sample, affecting the nature of the spectra.

To illustrate, it has been long recognized that the value of agricultural products such as cereal grains and the like are affected by the quality of their inherent constituent components. In particular, cereal grains with desirable protein, oil, starch, fiber, and moisture content and desirable levels of carbohydrates and other constituents can command a premium price. Favorable markets for these grains and their processed commodities have therefore created the need for knowing content and also various other physical characteristics such as hardness and "test weight" (bulk density). Accordingly, when a truck with a trailer load of grain arrives at a grain elevator, the elevator operator needs to obtain a good statistical sample of the grain in the truckload, and then measure the properties of the samples. From this sampling, the overall properties of the grain (such as protein, oil and moisture content) are estimated for the truckload. Fast measurement and immediate answers are desired so that the grain may be judged as acceptable or not, and if acceptable, directed to the proper storage location based on the measured characteristics. Current methods utilize a physical sampling probe, which is driven vertically down into the grain and mechanically or pneumatically withdraws samples from various depths. The withdrawn samples are then analyzed, e.g., by infrared techniques. However, the cost of labor and time for serially withdrawing individual samples and then processing the samples can limit the number of samples withdrawn from a given truckload of grain and therefore potentially hamper the ability to obtain good sampling statistics.

Another problem with on-site spectroscopic detection techniques can arise in situations where the analyte to be detected, e.g., fluids or particulates, is being transported across the field of vision of the spectral analyzer, such as in a chute or on a conveyor belt. For instance, an open fluid or particle "stream" having a varying cross-sectional dimension can present difficulties where it is necessary that some portion of the spectral probe be positioned at a fixed distance from the surface of the stream. To illustrate, the truckload of grain referred to above may transported from the truck to locations within the elevator facilities on conveyor belts, in some cases at speeds as fast as 10 feet/second. The unevenness of the stream of grain on the belt can be problematic to positioning a spectroscopy probe at a constant fixed distance from a surface of the grain stream. On the other hand, inserting the probe into the stream to maintain a constant distance between the probe head and the grain being analyzed may cause unacceptable turbulence in the flow of particles or fluid.

Moreover, in certain instances the fluid or particle stream may be fast enough that difficulties are encountered in obtaining enough measurements for good statistical sampling, particularly where the particle or fluid stream is heterogeneous in composition. Returning again to the example of the grain elevator, many of the transport processes which may be amenable to spectroscopic detection from the standpoint of accessibility to the grain, e.g., for placement of infrared probes and the like, may in fact be less than ideal due to the speed with which the grain would be transported by the field of vision of the probe. Grain being unloaded from a truck, for example, may be unloaded though delivery chutes at a rate of tens of bushels per second. In view of the potential heterogeneity in the grain being monitored, and the speed with which the grain is moving, providing good statistical sampling of the quality of the grain by spectroscopic techniques using a probe positioned along the flow path can be impaired by the lack of time to get an adequate number of sample spectra.

SUMMARY OF THE INVENTION

The present invention relates to spectral analysis systems and methods for determining physical and chemical properties of a sample by measuring the optical characteristics of its transmitted and/or reflected light. In general, the systems and methods of the present invention are useful for examining the spectroscopic characteristics of materials, such as particles or liquids, though the systems may be used to characterize other materials such as suspensions of particles and even gases. In certain embodiments, it is especially advantageous to use the subject system in connection with non-uniform material, e.g. consisting of components of different compositions, because the system of the present invention does not require the samples to be homogeneous in order to achieve reliable results.

However, in addition to characterizing heterogeneous materials, the subject systems can also be used to ascertain whether or when a mixture or a stream of material is sufficiently homogeneous or fulfils certain specifications with regard to content and/or particle size.

One aspect of the present invention relates to an insertion probe system for spectral analysis of flowable materials, or other materials, including static materials, into which a probe can be inserted, for which internal spectroscopic sampling is desired. In such embodiments, the invention provides a spectral analysis system including a probe which can be inserted into, e.g., bins, bales, vats, blenders, silos, mixers, drums, flow streams, and the like, of granular, powder or liquid matter and suspensions.

In general, the probe may include a probe head having: (i) a light source arranged to irradiate a sample volume of the material proximate the probe head, which source may be a lamp or other radiation source disposed in the probe head or it may be the radiant end of an optical fiber or other waveguide delivering light from a source distal to the probe head; and (ii) an optical pick-up, arranged to receive light energy reflected or otherwise emitted from a sample in the irradiated sample volume. The light source provides a suitably broad bandwidth of light for irradiating the sample, and in certain preferred embodiments, simultaneously irradiates at multiple wavelengths. The light pick-up receives light reflected or emitted from a sample being irradiated, and is in optical communication with one or more detectors which measure the intensity of the light reflected or emitted by the sample in a wavelength-dependent manner. Where the detector is located distal to the probe head, the pick-up may be an aperture in the probe head connected with an optical fiber or other waveguide which communicates light reflected or emitted by the sample to the detector. Where the detector is proximal to the irradiated sample, as it may be if disposed in the probe head, the pick-up may simply be an aperture for permitting light being reflected by the sample to enter the probe head. The system can also include one or more signal processing circuits, such as in the form of a computation subsystem, for processing signals from the detector.

A salient feature to certain preferred embodiments of the subject insertion probe relates to the sample volume irradiated by the probe. As described in further detail below, the irradiated sample volume can be shaped to be circumferential, or at least substantially circumferential, to the light source, and preferably to the long (insertion) axis of the probe. For instance, the probe may irradiate a toroidal sample volume wrapping circumferentially around the light source. Moreover, the sample volume is preferably disposed 180° to 360° circumferentially around the light source, and more preferably 270° to 360°, and even more preferably 360° around the light source. In certain embodiments, the irradiation pattern provides for an irradiation surface area of about 10 times $R^2$, and more preferably at least about 25 times $R^2$, at least about 50 times $R^2$, at least about 75 times $R^2$ or even at least about 100 times $R^2$, where R is the radius of the probe. By providing a larger sample volume, the advantages to such configurations of the system include the ability to collect data more likely to be statistically representative of a heterogeneous mixture and to get better signal-to-noise in the spectral analysis. Moreover, a larger sample volume permits a more efficient use of the light and helps to provide improved signal-to-noise.

Another aspect of the present invention relates to a variable surface probe system for spectroscopic analysis of a moving sample of a flowable material. In particular, the invention provides a spectral analysis system including a probe which can be variably positioned in contact with the moving surface of the material, or a fixed distance below the surface, without substantially disrupting the flow of the material. In such embodiments, the invention provides a spectral analysis system including a probe which can be inserted or placed on top of, e.g., moving material on a conveyor belt, grain belt, and the like.

In general, the probe may include a probe head having: (i) a light source arranged to irradiate the flowable material proximate the probe head, which source may be a lamp or other radiation source disposed in the probe head or it may be the radiant end of an optical fiber or other waveguide delivering light from a source distal to the probe head; (ii) an optical pick-up, arranged to receive light energy reflected or otherwise emitted from a sample in the irradiated sample volume; (iii) a planing element which permits the probe head to skim the surface of the flowing material when in contact; and, optionally, (iv) a constant force generator which applies a force to the probe head to maintain a constant amount of contact between the probe and the sample. The planing element of the probe may be, merely to illustrate, convex or concave such that when contacted with the surface of the moving material, e.g., at a shallow angle of attack, the planing element allows the probe to traverse the flowing material without creating significant turbulence in the material. The light source provides a suitably broad bandwidth of light for irradiating the sample, and in certain preferred embodiments, simultaneously with multiple radiation wavelengths. The light pick-up receives light reflected or emitted from a sample being irradiated, and is in optical communication with one or more detectors which measure the intensity of the reflected light, e.g., in a wavelength-dependent manner. Where the detector is located distal to the probe head, the pick-up may be an aperture in the probe head connected with an optical fiber or other waveguide which communicates light reflected or emitted by the sample to the detector. Where the detector is proximal to the irradiated sample, as it may be if disposed in the probe head, the pick-up may simply be an aperture for permitting light being reflected by the sample to enter the probe head. The system can also include one or more signal processing circuits, such as in the form of a computation subsystem, for processing signals outputted from the detector.

Still another aspect of the present invention relates to a multihead probe system for spectroscopic analysis of a moving sample of a flowable material. In such embodiments, the invention provides a spectral analysis system including a probe which can be inserted into a fast moving flow, e.g., a truck discharging its load at a grain elevator. It may be used in any granular solid or liquid or gas that moves through or along a passage, either enclosed or open. This could include manure, soil, sludge, mining materials, raw and fine chemicals, pharmaceuticals, food stuffs, waste materials, hazardous waste, petroleum and its products, commercial gaseous products, stack gases, etc.

In particular, the invention provides a spectral analysis system including a plurality of probe heads, e.g., which are simultaneously (relative to each other) able to irradiate and collect spectral information on the moving sample. In general, each of the plurality of probes may include a probe head having: (i) a light source arranged to irradiate the flowable material proximate the probe head, which source may be a lamp or other radiation source disposed in the probe head or it may be the radiant end of an optical fiber or other waveguide delivering light from a source distal to the probe head; and (ii) an optical pick-up, arranged to receive light energy reflected or otherwise emitted from a sample in the irradiated sample volume. Each light source provides a suitably broad bandwidth of light for irradiating the sample, and in certain preferred embodiments, the light sources may simultaneously irradiate the sample with multiple radiation wavelengths, e.g., each light source may provide light at a distinct wavelength. The light pick-up receives light reflected or emitted from a sample being irradiated, and is in optical communication with one or more detectors which measure the intensity of the reflected light, e.g., in a wavelength-dependent manner. Where the detectors are located distal to the probe head, the pick-up may be an aperture in the probe head connected with an optical fiber or other waveguide which communicates light reflected or emitted by the sample to the detector. Where the detector is proximal to the irradiated sample, as it may be if disposed in the probe head, the pick-up may simply be an aperture for permitting light being reflected by the sample to enter the probe head. The system can also include one or more signal processing circuits, such as in the form of a computation subsystem, for processing signals outputted from the detector.

Still another aspect of the invention relates to a probe system for spectroscopic analysis of a sample material that minimizes the effects of surface reflection on the spectral analysis of the sample thereby improving the spectral analysis. In such embodiments, the invention provides a probe system for spectral analysis in industrial, drug manufacturing, chemical and petrochemical settings and the like. In one particular embodiment, the probe is used in situations with sample materials having a large component of surface reflections relative to light paths passing through particles or a bulk of sample material in a diffuse, scattering path.

In particular, the invention provides a probe head for use with a spectrometer to analyze a material, the probe head having: (i) a light source arranged to irradiate a sample volume of the material proximate the probe head, which source may be a lamp or other radiation source disposed in the probe head; (ii) an optical pick-up, arranged to receive light energy reflected or otherwise emitted from the sample in the irradiated sample volume and transmit the emitted light to the spectrometer for analysis; (iii) an optical blocking element positioned within the optical path between the light source and the optical pick-up to force the optical path into the sample volume; and (iv) a reference shutter for selectively blocking light emitted from the irradiated sample volume from reaching the optical pick-up to facilitate calibration. The optical blocking element minimizes direct surface reflections from the sample or from components of the probe head, such as, for example, a sample window positioned in contact with or proximate the material, relative to light passing through and reflecting from the material within the sample volume to thereby improve the accuracy of the analysis of the material. The light source provides a suitably broad bandwidth of light for irradiating the sample, and in certain preferred embodiments, simultaneously with multiple radiation wavelengths. The light pick-up receives light reflected or emitted from a sample being irradiated, and is in optical communication with one or more detectors which measure the intensity of the reflected light, e.g., in a wavelength-dependent manner. Where the detector is located distal to the probe head, the pick-up may be an aperture in the probe head connected with an optical fiber or other waveguide which communicates light reflected or emitted by the sample to the detector. Where the detector is proximal to the irradiated sample, as it may be if disposed in the probe head, the pick-up may simply be an aperture for permitting light being reflected by the sample to enter the probe head. The system can also include one or more signal processing circuits, such as in the form of a computation subsystem, for processing signals outputted from the detector.

In one embodiment of the subject method, the composition of the inspected material can be quantified by detecting molecular vibrational modes characteristic of one or more constituents of the material, as for example proteins, lipids, fatty acids, etc. This aspect of the method comprises irradiating the sample with electromagnetic radiation, e.g., infrared radiation, e.g., preferably near infrared radiation, in a wavelength range which is converted by the sample into molecular vibrations, e.g., in the wavelength range of infrared radiation, and measuring at least one of an absorption or transmission of the electromagnetic radiation by the sample. Infrared radiation refers broadly to that part of the electromagnetic spectrum between the visible and microwave regions. This encompasses the wavelengths from about 700 nm to about 50,000 nm. Near infrared radiation includes wavelengths in the range of about 700–2500 nm. For instance, it has been discovered that protein levels in grains can be determined by measuring near infrared absorption at particular wavelengths. As used herein, the term "near infrared" or "near IR" is intended to encompass light in a spectrum ranging from about 700 to about 2500 nm, more preferably from about 1300 to about 2400, and, in some instances, most preferably from about 1400 to about 2200 nm.

In certain preferred embodiments, the subject systems and methods measure a spectral response to short wavelength, near infrared (NIR) radiant energy in the range 700–2500 nm, and even more preferably from 600 to about 1100 nanometers (nm). The system may also be set up to irradiate the sample in the visible spectrum, including wavelengths as low as about 400 nanometers (nm). The spectral response at shorter wavelengths helps in the modeling of proteins and other constituents in conjunction with the response at higher wavelengths, and be useful in those embodiments where grains or other protein-containing materials are being characterized.

Although the infrared spectrum is characteristic of the entire molecule, certain groups of atoms give rise to bands at or near the same frequency regardless of the structure of the rest of the molecule. It is the persistence of these characteristic bands that permits the practitioner to obtain useful structural information by simple inspection and reference to generalized charts of characteristic group frequencies. To illustrate, the conjugated diketone is a structure that is likely to be persistent irrespective of the length of a fatty acid. Furthermore, other chemical structures of proteins, fatty acids and other natural constituents have been determined that and are suitable for detection by infrared means.

Infrared radiation of frequencies less than about 100 cm$^{-1}$ (wavelengths longer than 10,000 nm) can be absorbed and converted by a constituent of the sample into energy of molecular rotation. This absorption is quantized; thus a molecular rotation spectrum can consist of discrete lines. Infrared radiation in the range from about 10,000–100 cm$^{-1}$ (1000 nm–10,000 nm) can be absorbed and converted by the sample into energy of molecular vibration. This absorption is also quantized, but vibrational spectra appear as bands rather than as lines because a single vibrational energy change can be accompanied by a number of rotational energy changes. The frequency or wavelength of absorption depends on the relative masses of the atoms, the force constants of the bonds and the geometry of the atoms in the fatty acid.

Band positions in infrared spectra are presented either as wavenumbers or wavelengths and are understood to be equivalent. The wavenumber unit (cm$^{-1}$, reciprocal centimeters) is used most often since it is proportional to the energy of the vibration and since most modern instruments are linear in the cm$^{-1}$ scale. Wavelength, $\lambda$, is referred to herein in terms of micrometers ($\mu$m, 10$^{-6}$ meters) or nanometers (nm, 10$^{-9}$ meters). Wavenumbers are reciprocally related to wavelength, e.g., 1/$\lambda$.

Band intensities can be classically expressed either as transmittance (T) or absorbance (A), though for the purpose of this application both of will be understood as within the meaning of the term "absorbance" or "absorption". As used in the art, transmittance is the ratio of the radiant power transmitted by a sample to the radiant power incident on the sample, and absorbance is the logarithm, to the base 10, of the reciprocal of the transmittance ($A=\log_{10}(1/T)$). The term absorbance or absorption further include scattered light, such as measured in Raman spectroscopy.

Moreover, other forms of vibrational spectroscopy, such as Raman spectroscopy, can be used as part of the subject methods. The Raman vibrational spectrum of these molecules can consist of a series of sharp lines which constitute a unique fingerprint of the specific molecular structure. Raman spectroscopy presents a means of obtaining vibrational spectra, especially over optical fibers, with visible or near infrared light, and provides a viable alternative to infrared spectrophotometry for use in the subject methods. These wavelength regions are efficiently transferred without significant absorption losses over conventional optical fiber materials. In Raman spectroscopy, monochromatic light is directed onto a sample and the spectrum of the scattered light is determined. However, due to a very weak signal, the excitation light must be quite intense, though laser light sources are readily available. In addition, optical filtering is necessary to separate the weak scattered signal from the intense Rayleigh line.

In yet another embodiment of the subject method, the constituents of a sample are determined in the sample by detecting molecular electronic modes characteristic of such constituents. This aspect of the method includes irradiating the sample with electromagnetic radiation, e.g., ultraviolet-visible radiation, e.g., ultraviolet radiation, in a wavelength range converted by the sample into electronic vibrations/ electron orbital transitions, e.g., in the wavelength range of 200–400 nm, e.g., at a wavelength of 275 nm and measuring the absorption of the electromagnetic radiation by the sample. In the ultraviolet and visible region of the spectrum, molecular absorption is dependent on the electronic structure of the molecule. Absorption of energy is quantized, resulting in the elevation of electrons from the ground state to higher energy orbitals in an excited state. For many electronic structures, the absorption does not occur in the readily available portion of the ultraviolet region.

There is, however, an advantage to the selectivity of ultraviolet absorption: characteristic groups can be recognized in molecules of widely varying complexities. As a large portion of a relatively complex molecule can be transparent in the ultraviolet region, a spectrum can be obtained similar to that of a much simpler molecule.

Wavelengths in the ultraviolet region of the spectrum are usually expressed in nanometers or angstroms (Å). The near ultraviolet (quartz) region includes wavelengths of 200–380 nm. The atmosphere is transparent in this region and quartz optics may be used to scan from 200 to 380 nm. Atmospheric absorption starts near 200 nm and extends into the shorter-wavelength region (10–200 nm), which is accessible through vacuum ultraviolet spectrometry.

The total energy of a molecule is the sum of its electronic energy, its vibrational energy, and its rotational energy. Energy absorbed in the ultraviolet region produces changes in the electronic energy of the molecule. These transitions consist of the excitation of an electron from an occupied orbital (usually a non-binding p or binding π-orbital) to the next higher energy orbital (an antibonding, π* or σ*, orbital). The antibonding orbital is designated by an asterisk.

Since ultraviolet energy is quantized, the absorption spectrum arising from a single electronic transition should consist of a single, discrete line. A discrete line is not obtained since electronic absorption is superimposed on rotational and vibrational sublevels. The spectra of simple molecules in the gaseous state consist of narrow absorption peaks, each representing a transition from a particular combination of vibrational and rotational levels in the electronic ground state to a corresponding combination in the excited state. At ordinary temperatures, most of the molecules in the electronic ground state will be in the zero vibrational level; consequently, there are many electronic transitions from that level. In molecules containing more atoms, the multiplicity of vibrational sublevels and the closeness of their spacing cause the discrete bands to coalesce, and broad absorption bands or "band envelopes" are obtained.

The principal characteristics of an absorption band are its position and intensity. The position of absorption corresponds to the wavelength of radiation whose energy is equal to that required for an electronic transition. The intensity of absorption is largely dependent on two factors: the probability of interaction between the radiation energy and the electronic system and the difference between the ground and the excited state. The probability of transition is proportional to the square of the transition moment. The transition moment, or dipole moment of transition, is proportional to the change in the electronic charge distribution occurring during excitation. Intense absorption occurs when a transition is accompanied by a large change in the transition moment. Absorption with $\epsilon_{max}$ values$>10^4$ is high-intensity absorption; low-intensity absorption corresponds to $\epsilon_{max}$ values$<10^3$.

Accordingly, the subject method relies on optically detecting individual chemical groups of a constituent of a sample which have been determined to be reliable as indicators for quantitatively determining the level of the constituent in the sample.

In one embodiment, the method comprises utilizing one of the subject systems for illuminating (e.g., irradiating) the sample at a plurality of discrete wavelengths, e.g. selected from the infrared, visible or ultraviolet spectrum. In certain embodiments, the wavelengths the sample is irradiated with include at least one sample wavelength and one reference wavelength. The sample wavelength is defined as being a wavelength for detecting a chemical feature whose existence is dependent on the presence of a constituent in the sample. The reference wavelength, on the other hand, is selected as a frequency which is not absorbed by the sample in a manner dependent on the presence of the constituent. Measurements of the intensity of transmitted, absorbed, or reflected light at such wavelengths are taken, and an analysis of transmittance, absorbance, or reflectance ratios for various wavelengths is performed.

In preferred embodiments, the reference wavelength is closely spaced and can be chosen so as to provide a "baseline" for determining the intensity of the peak of interest, such as the band intensity of a peak arising due to the constituent. Changes in the ratios can be correlated from the sample wavelength, which obviously will vary with the state amount of the constituent in the sample, and the second (reference) wavelength, which is sufficiently removed from the sample wavelength so that measurements of light absorption at this second wavelength is relatively insensitive to the concentration of the constituent, and yet which is sufficiently close to the first wavelength to minimize interference from scattering effects and the like. Typically, the window bracketing these closely spaced wavelengths will be less than about 300 nm and preferably less than about 60 nm wide and, in some instances, more preferably less than about 30 nm wide. The reference wavelength can be chosen so as to detect a chemical feature which remains relatively unchanged (e.g. does not change in significant manner) as the normal makeup of the sample changes, or can be selected as a wavelength which does not correspond to any sharp absorption bands but which provides baseline correction to compensate for convoluted or "rolling" baselines.

As will be understood, there are a wide variety of materials for which the systems and methods of the present invention can be used for characterization. Without intending to be limiting, exemplary materials include:

vegetable foods, such a wheat, corn, rye, oats, barley, soybeans, amaranth, triticale, and other grains, rice, coffee and cocoa, which may be in the form of whole grains or beans, or a ground or comminuted product (analysis for protein, starch, carbohydrate and/or water), seeds, e.g. peas and beans, such as soybeans (analysis for protein, fats and/or water), products mainly consisting of or extracted from vegetable raw materials, such as snacks, dough, vegetable mixtures, margarine, edible oils, fibre products, chocolate, sugar, syrup, lozenges and dried coffee extract (powder/granulate), animal foodstuffs, such as dairy produce, e.g. milk, yogurt and other soured milk products, ice cream, cheese (analysis for protein, carbohydrate, lactose, fat and/or water), meat products, e.g. meat of pork, beef, mutton, poultry and fish in the form of minced or emulgated products (analysis for protein, fat, water and/or salts) and eggs, which foodstuffs may be present in a completely or partly frozen condition, fermentation broths, such as alcoholic beverages, e.g. wine or beer, fodder, e.g. pellets or dry/wet fodder mixtures of vegetable products, fats and protein-containing raw materials, including pet food, manure and compost, including composting garbage, grass clippings, pharmaceutical products, such as tablets, mixtures, powders, creams and ointments, biological samples including, for example, biological fluids such as blood, urine, spinal fluid, saliva, etc, and tissue samples, and technical substances, e.g. wet and dry mixtures of cement and mortar, plastics, e.g. in granular form, mineral materials, such as solvents and petro-chemical products, e.g. oils, hydrocarbons and asphalt, solutions of organic or inorganic substances, e.g. sugar solutions, glue and epoxies, and liquids with light scattering properties in suspension, slurries, fluidized materials including both solid and liquid and similar entities.

The components comprising the systems of the present invention are preferably integrated into a single unit, e.g., to create either a portable spectral analyzer or one which is readily disposed along a path of a moving material.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 6b and 6c are cross sectional views of embodiments of the planing element of the optical probe of FIG. 6a;

FIG. 7b is a cross-sectional view of the multiple probe head apparatus of FIG. 7a;

DETAILED DESCRIPTION OF THE INVENTION

I. Overview

Figure 1:
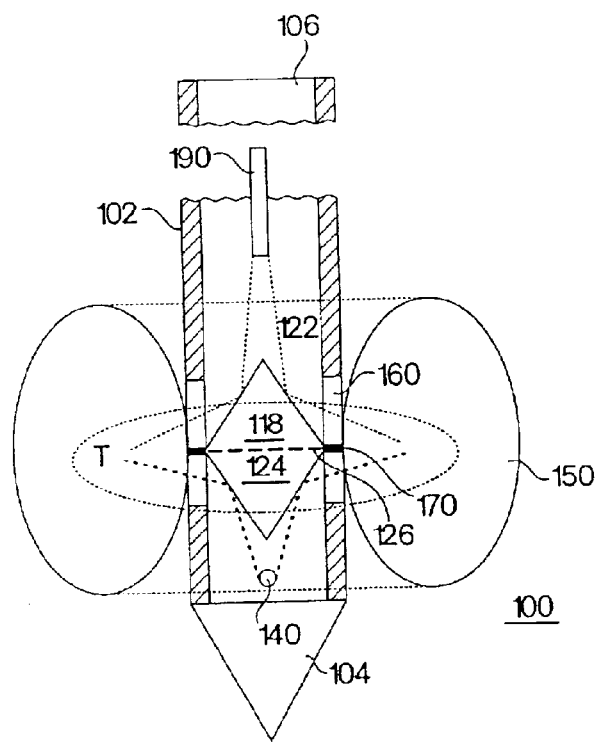
FIG. 1 is a schematic representation, in cross-section, of an optical probe for insertion into a flowable sample material, according to the present invention.

One aspect of the invention provides a probe for insertion into a flowable material. An exemplary use of the subject probe is in the analysis of grain. To illustrate, it has been long recognized that the value of agricultural products such as cereal grains and the like are affected by the quality of their inherent constituent components. In particular, cereal grains with desirable protein, oil, starch, fiber, and moisture content and desirable levels of carbohydrates and other constituents can command a premium price. When a truck with a trailer load of grain arrives at a grain elevator, the elevator operator needs to obtain a good statistical sample of the grain in the truckload, and then measure the properties of the samples. The present invention provides a probe assembly which eliminates the need for physical sampling of the grain. Rather, the grain is examined spectroscopically while it is still in the truck or other container. One feature of the probe pertains to the shape of the output light, e.g., the sample volume. As described in further detail below, the irradiated sample volume can be shaped to be circumferential, or at least substantially circumferential, to the light source, and preferably to the long (insertion) axis of the probe. By providing a larger sample volume, the advantages to such configurations of the system include the ability to collect data more likely to be statistically representative of a heterogeneous mixture and to get better signal-to-noise in the spectral analysis.

Another aspect of the invention relates to a probe system optimized for a variable surface for spectroscopic analysis of a moving sample of a flowable material. The present invention provides a probe assembly which eliminates the need for physical sampling of the grain. Rather, the grain is examined spectroscopically while it is on a conveyor belt or similar apparatus.

Another aspect of the invention relates to multiple probe assemblies for obtaining spectral information from flowing materials. As set out in the background, the methods used to unload and transport materials such as grain at elevator facilities can have very high throughput. Where multiple measurements may be required to obtain good sampling statistics, the present invention contemplates the use of multiple probe assemblies to permit simultaneous acquisition of spectral data from several points in the material, whether those points be in the same stream (e.g., the same chute from a truck) or in different streams (e.g., from different chutes from a truck). The use of the subject multiple probe systems can be particularly important for analyzing heterogeneous materials which may have undergone separation, e.g., such as the dynamical separation process which can occur in the storage container during the movement of material.

Another aspect of the invention relates to a probe optimized for measurement of material which has a large component of surface reflections relative to light paths passing through the particles of bulk of the material in a diffuse, scattering path. Measurements may be required in mixing vats and the like, for example, a measurement in a vat of a pharmaceutical mixture of an active substance and an inactive substance or filler, both of which may have a large component of surface reflections. The present invention contemplates the use of a probe for measuring the spectra of a such a mixture using preexisting window in the vat or other container. The use of the subject probe can be particularly important for analyzing the amount of dispersion of an active ingredient within a inert or inactive ingredient, or quantifying the heterogeneity of such a mixture.

All aspects of the current invention include a probe which has the capability of simultaneously forcing the optical path via an optical block, together with a reference shutter or similar aspect which offers easy quality control and updates the systems' instrument calibration.

II. Definitions

For convenience, the meaning of certain terms and phrases employed in the specification and appended claims are provided below.

The term "light" as used herein refers to radiant electromagnetic energy which may be in the visible or non-visible wavelength(s) range, which is detectable by spectroscopic techniques. The term includes radiant energy at visible, infrared and ultraviolet frequencies.

As used herein, the terms "spectrophotometric" and "spectroscopic" are used interchangeable and refer to the spectral properties of a sample, such as the degree to which the sample transmits or reflects electromagnetic radiation at certain frequencies. The systems and methods of the present invention can employ, for example, UV-VIS spectroscopy, IR spectroscopy or Raman spectroscopy to determine the spectroscopic characteristics of a sample.

The expression "near-infrared spectroscopy" is used to designate methods of measurements based upon the interaction between matter and electromagnetic radiation in the wavelength range from 700 to 2500 nm. The reason for using this expression is that it refers to the part of the infrared wavelength range lying closest to the visual range of the spectrum (400 to 700 nm). In the literature, the expression "near—near-infrared range" is used for electromagnetic radiation with wavelengths from 700 to 1200 nm.

Near-infrared spectroscopy can be used in the subject systems for determining components of various materials, e.g. proteins, nucleic acids, fatty acids and water to name but a few. Each type of chemical bond such as O—H, C—H, C=O, C—N, N—H, absorbs light at wavelengths characteristic for the molecule part concerned. The cause of the absorption is that two different atoms being bonded to each other function in the manner of an electric dipole taking energy from the electric and magnetic fields in the radiation, making the group of atoms concerned vibrate. Thus, a C=O bond in a triglyceride will absorb light at a wavelength, that is different from that absorbed by a C=O bond in a protein molecule. By measuring how much the light is changed by passing through a sample at multiple wavelengths, it is possible to determine the percentage of a component of the sample.

III. Exemplary Embodiments

Referring to the insertion probe embodiment of the present invention, there is provided a probe head 100, as shown in FIG. 1, for spectroscopic measurement of properties of matter, for instance grain. The probe head 100 includes a shaft 102 having a distal end 104 spaced apart along the longitudinal axis of the shaft from a proximal end 106. The probe head 100 is designed to be inserted into a material to create a flow of material past and around the probe head during spectroscopic analysis to facilitate rapid and accurate analysis of the material. To this end, the shaft 102 and the distal end 104 of the probe head 100 preferably are adapted to penetrate and travel in a mass of flowable material, such as, grain, by optimizing the shape of the shaft 102 and the distal end 104 to minimize turbulence within the material when the probe head is inserted into the material. For example, the shaft 102 can be cylindrical in shape, having a circular cross-section, and the distal end 104 can have a conical shape that tapers to a point to form an insertion point for the probe head 100, as illustrated in FIG. 1. One skilled in the art will recognize, however, that the shaft 102 can be constructed with alternative cross-sectional shapes, such as, for example, elliptical, oval, or rectilinear, without departing from the scope of the present invention. In addition, one skilled in the art will appreciate that the shaft 102 can have a non-uniform cross-section, although a uniform cross-section is preferred, as illustrated in FIG. 1, to minimize turbulence in the sample material. Likewise, the distal end 104 of the shaft 102 is not limited to the conical shape illustrated in FIG. 1. The distal end 104 can be constructed having alternative shapes selected to minimize turbulence or wear as the probe head is inserted into the sample material.

The shaft 102 may be made of metals such as stainless steel, steel or aluminum; or made from moldable and durable plastic; or other materials. The materials may be chosen for ease of cleaning and maintenance. The shaft 102, including the distal end 104, can also be constructed of material which optimizes the appropriate measurements of the sample material. To further optimize the flow of material as the probe head 100 is inserted, the probe head shaft 102 and ends 104 and 106 are preferably constructed from materials, or coated with a material, to minimize friction between the probe surface and sample material.

The probe head 100 may also include an upper window 160 and a lower window 130 positioned circumferentially about the cylindrical shaft 102. Each of the windows can be formed of a suitable material, such as sapphire or glass, which is transmissive at the wavelengths of interest, and which does not see a significant absorption shift due to temperature changes. Sapphire also resists scratching and, therefore, debris brushing against its surface will not damage the window.

In one embodiment, a light source 140 may be placed within the cylindrical shaft 102 between the distal end 104 and the lower window 130. The source may be, for example, a hot filament of a white light bulb, or any other material capable of generating light. In other embodiments, the light source can be a number of (power) laser diodes, each emitting light of a respective wavelength. Typically, multiple (e.g., 4–20) diodes can be placed on the same chip. Each laser diode emits light over a small range of wavelengths within the range from 800–1050 nm. In certain instances, e.g., where the laser has a small irradiation area, it may be desirable to include a lambertian diffuser through which the laser light passes, in order to provide the wide angle irradiation contemplated for the subject probe.

The probe head 100 may also include an optical pick-up, 190, arranged to receive light emitted from the sample in the irradiated sample volume 150 and transmit the received light to, for example, a spectrometer, for analysis. The optical pick up 190 can be an aperture, a waveguide, an optical fiber or any other optical element suitable for transmitting light for analysis.

Adjacent to the light source 140 is a reflector 118, which may be secured within the cylindrical shaft 102 against an optical blocking element 170, discussed below, separating the upper window 160 from the lower window 130. The reflector 118 includes a first reflective surface 120 that reflects and shapes the light output from the light source 140 through the lower window 130, so that when the probe head 100 is inserted into matter of which the properties are to be measured, the output from the light source 140 may be caused to diffuse from the shaft 102 into the matter surrounding the probe head 100.

The pattern of light diffusion from the shaft 102, in one embodiment, is illustrated in FIG. 1 as a cross section of a torus 150. Such a pattern may be generated when light from the light source 140 diffuses from the lower window 130 into the surrounding matter and some of the diffused light is reflected back through the upper window 160 on the shaft 102. It should be noted that the light entering the shaft 102 through the upper window 160 may be optically separated and optically blocked from the lower window 130 by the optical blocking element 170. Light entering through the upper window 160 may be reflected and concentrated by a second reflective surface 180 of reflector 118 to the optical pick-up 190, in this exemplary embodiment, a light collecting optical fiber 190 positioned within the cylindrical shaft 102. The optical fiber 190 may be a single fiber or a plurality of fibers with or without special shaping to the tip or inclusion of lens(es) at the tip and may be connected to an NIR spectrometer and analysis system 106, so that the collected light may be transported thereto for analysis.

The reflective surfaces 120 and 180 of the reflector 118 may be made of any reflective material and may be oriented at any angle suitable for guiding light from the light source into the sample material (reflective surface 120) and for guiding light reflected from the material (reflective surface 180). As discussed in detail below, the angle of the reflective surfaces 120 and 180 can be selected to optimize the size and shape of the sample volume and, thereby, maximize the accuracy of the spectral analysis. In the exemplary embodiment illustrated in FIG. 1, the reflector 118 is diamond-shaped in cross-section and is composed of two cone-shaped halves 122 and 124, each having an outer surface that forms one of the reflective surface 180, 120, respectively. The upper cone-shaped half 122 is inverted and contacts the lower cone shaped-half 124 such that the bases of the cone-shaped halves meet along a center line 126 of the reflector 118. Thus, a plane oriented perpendicular to the axis of the shaft 102 and passing through the center line 126 of the reflector 118 is a generally circular in shape. The reflector 118 can have a unitary construction, as illustrated in FIG. 1, or can be constructed from multiple components connected to form a single reflector or separated such that the reflective surfaces 120 and 180 are provided on two or more independent reflectors. One skilled in the art will appreciate that the size and shape of the reflector 118 can be varied to provide the optimal size, shape, and orientation of the reflective surfaces 120, 180.

In a preferred embodiment, the optical fiber 190 and the light source 140 are arranged on a common axis that is parallel to the longitudinal axis of the shaft 102. One skilled in the art will appreciate that the optical fiber 190 and the light source 140 can be positioned along an axis that is oriented at an angle from the longitudinal axis or the shaft 102. In addition, the distance between the light source 140 and the optical fiber 190, as well as the reflector 118, can be varied and is preferably selected to optimize the size and shape of the sample volume being analyzed.

As discussed above, the upper window 160 and the lower window 130 may be separated by an optical blocking element, such as light-blocking ring 170 in the exemplary embodiment illustrated in FIG. 1. The light-blocking ring 170 is preferably made of an opaque material and is provided to discriminate against surface reflection from the material being probed and from the upper window 160 and the lower window 130 by forcing the path length of the light into the sample material being analyzed. The thickness, t, shown in FIG. 1 of the light-blocking ring 170 can be varied according to the optical characteristics of the material being probed and is preferably selected to maximize the accuracy of the spectral analysis by blocking and, thus, inhibiting surface reflections from reaching the optical pick-up 190. One skilled in the art will appreciate that the light blocking element 170 is optional, as in certain embodiments the influence of direct surface reflections on the accuracy of the spectral analysis may not be a concern.

Figure 2:
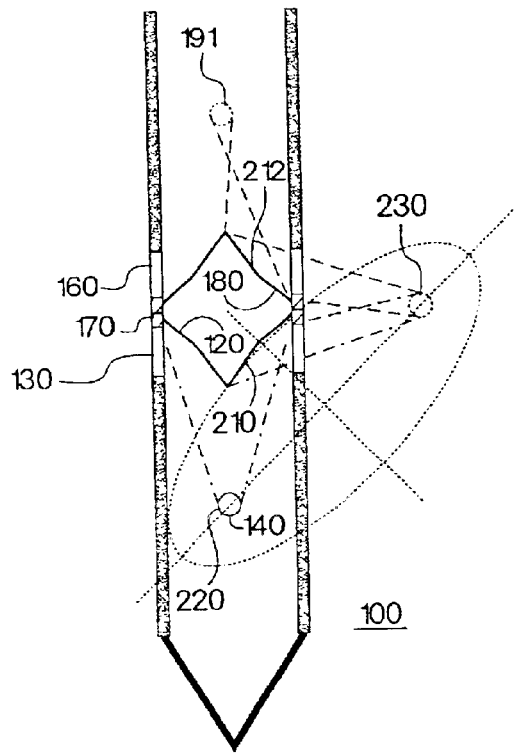
FIG. 2 is a schematic representation, in cross section, of an optical probe including an elliptical reflector, according to the present invention.
Figure 5A:
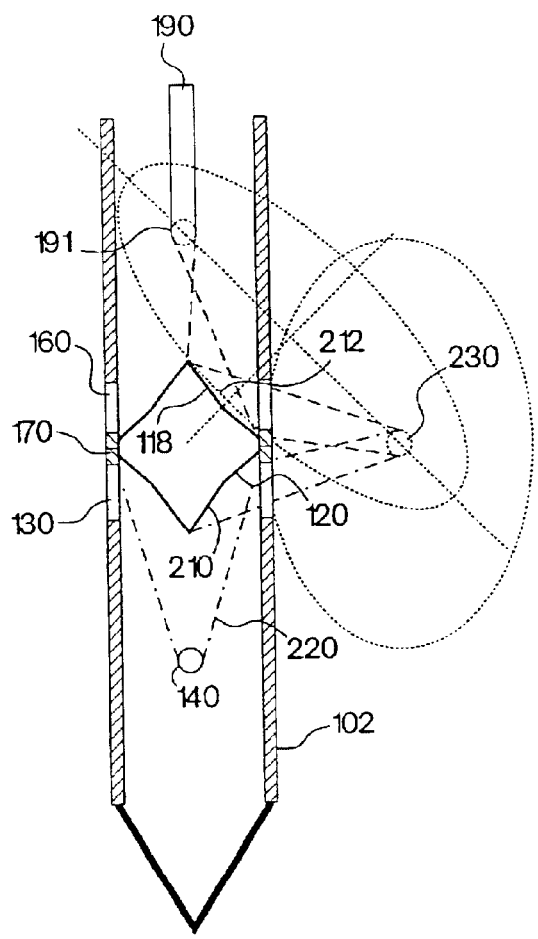
FIGS. 5a and 5b are schematic illustrations of a method of determining the shape of the elliptical surface of the elliptical reflector of the probe head of FIG. 2.
Figure 5B:
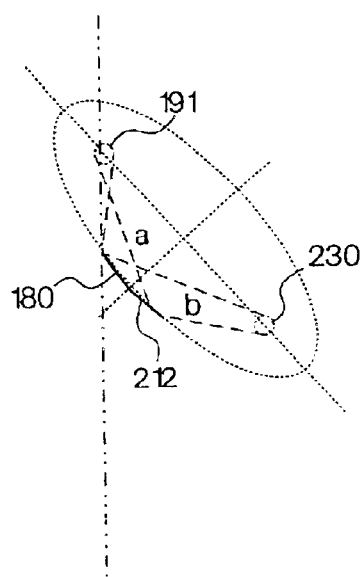

Referring now to FIG. 2, in order to provide a pattern of light diffusion and reflection to permit optimal collection and measurement, the reflective surface 120 and the reflective surface 180 may be configured so that its optical surface may correspond to a revolution of a section of an ellipse 210. It is well known from optical geometry that light rays from one focal point of an ellipse will reflect to the other focal point of an ellipse. Therefore one of the optimal shapes of the reflector surfaces 120 and 180 is a shape which corresponds to an ellipse. The equation of an ellipse which governs this relationship is $$\left(\frac{x}{a}\right)^2 + \left(\frac{y}{b}\right)^2 = 1$$

where a is the distance from one focal point to a point on the ellipse surface, and b is the distance from the other focal point to the same point on the ellipse surface, as best illustrated in FIGS. 5a–5b. This equation also describes the optimal surface for the reflective surfaces 120 and 180. For a given material, the optimal focal points in the material may change, and thus change the parameters a and b in the equation above.

The ellipse 210, in one embodiment, preferably has one of its foci 220 at the light source 140 and another 230 at a diffusion length into the sample at a level of symmetry, e.g., substantially equivalent to the height of the block 170. An analogous ellipse 212, has a foci 191 at the tip of the fiber and a second foci 230 at a diffusion length into the sample, as best illustrated in FIGS. 5a–5b. Thus, the geometry or shape of the reflective surfaces 120 and 180 preferably corresponds to the surface of ellipse 210 and ellipse 212, respectively. In certain embodiments, the reflective surfaces 120 and 180 may be approximated by one or more straight lines or one or two sections of a circle, for ease of manufacture.

Alternatively, the reflective surfaces 120 and 180 may approximate polar symmetry by being a section of a square, hexagon, octagon or other polygon, so long as such configuration provides a pattern of light diffusion and reflection to permit optimal collection and measurement.

Figure 3:
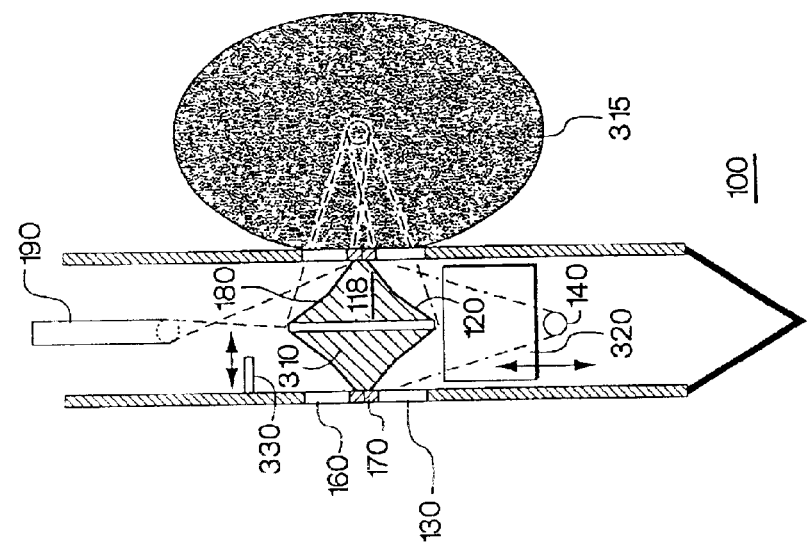
FIG. 3 is a schematic representation, in cross-section, of an optical probe head including an elliptical reflector and a cylindrical shutter, according to invention.

Referring to FIG. 3, the probe head 100 may be provided with a passage 310 through the reflector 180 so that light directly from the source 140 may be collected by the optical fiber 190 for calibration. The passage 310 may be an open tube, and may include reflecting walls, or may be an optical fiber or a plurality of fibers. In one embodiment, the passage 310 is provided with a first shutter 330 which may close the passage 310, except during calibration, so that during measurement of the material 315, light directly from the source 140 may be prevented from reaching the optical fiber 190. During calibration, the first shutter 330 can be moved into an open position, as shown in FIG. 3, while a cylindrical second shutter 320 may be slid into a first position over the lower optical window 130 to prevent any diffused light reflected from the material 315 being measured from reaching the collecting optical fiber 190. In this manner only direct light from the source 140 can reach the collecting optical fiber 190 for calibration. The second shutter 320 may be slid into a second position, shown in FIG. 3, wherein the lower optical window 130 may be exposed to permit light from the source 140 to diffuse into the material 315 being measured and reflected toward the collecting optical fiber 190 via reflective surface 180. Alternatively, the second shutter 320 may be moved into a position over the upper optical window 160 to prevent any light from the matter 315 from reaching the optical fiber 190. In an another embodiment, the second shutter 320 may be slid into a position over both windows 130 and 160 for a "dark" calibration measurement, as discussed in more detail below.

Figure 4:
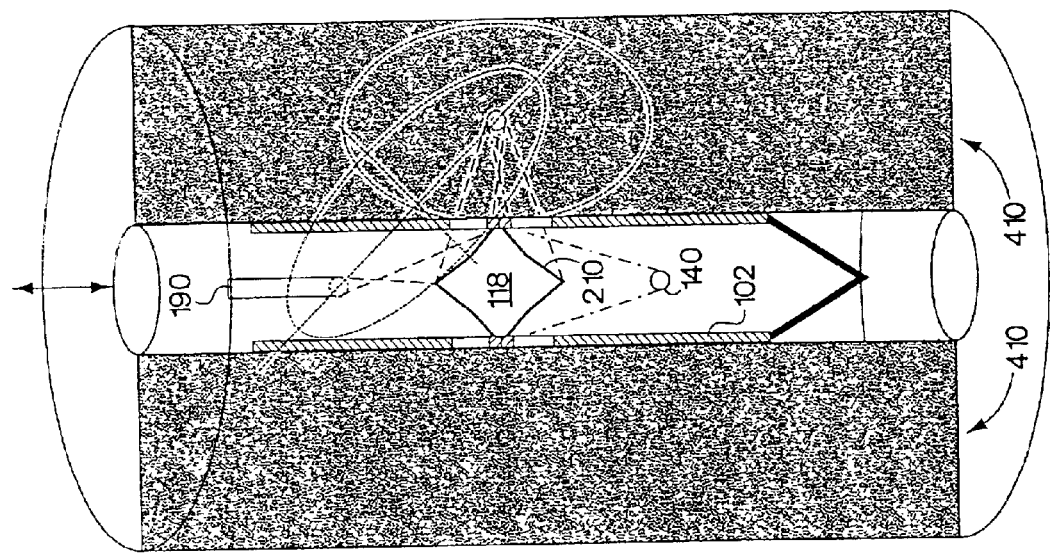
FIG. 4 is a schematic representation of the probe head of FIG. 3, illustrating the probe head inserted within a flowable sample material.

The probe head 100, in accordance with an embodiment of the present invention, can generate a light output which can significantly increase the volume of material sampled. The volume of material that may be sampled may, to a certain extent, be dependent on the strength of the output from the light source 140 in the radial direction, and the scale length of diffuse scattering and absorption in the matter being measured for the wavelengths in use. The volume sampled, however, need not be limited circumferentially, as the probe can be configured to permit light output from the light source 140 to diffuse from the probe head 100 approximately 360° about the shaft 102, as illustrated in FIG. 1. Thus, as the probe head enters or is withdrawn from a volume of matter being measured, the volume of material which may be measured is substantially a cylindrical donut shape volume 410, as illustrated in FIG. 4.

In certain embodiments, the probe head 100 and windows 130 and 160 can be adjusted or blocked to direct the output from source 140 in a range of angles from 0° to 360° circumferentially about the shaft 102. For example, portions of the both windows 160 and 130 can be opaque to manipulate the angles of measurement about the shaft. Alternatively, portions or all of the reflective surfaces 120 or 180 can be blocked, for example, with an opaque material or coating or formed from a non reflecting material, to direct the output from source 140 at selected angles circumferentially about the light source 140.

In certain embodiments, the upper window 160 can include a diffuser in the path of the light received from the irradiated sample to ensure that only spectral information is measured without imaging of the sample.

Figure 6A:
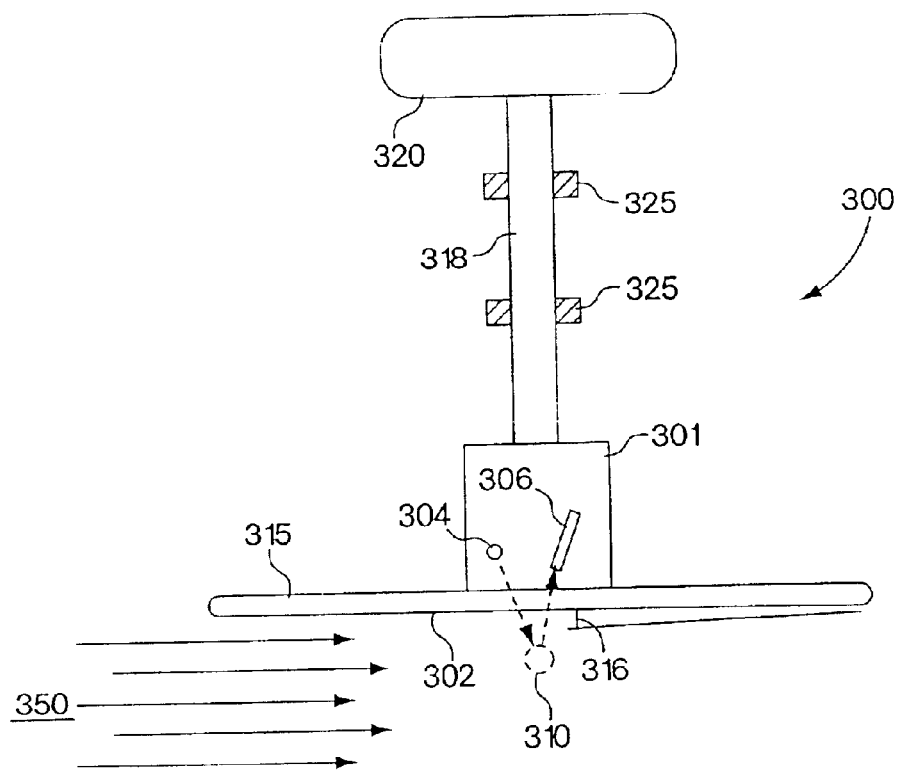
FIG. 6a is a schematic illustration of an optical probe having a planing element for contacting a stream of flowable material, according to the present invention.
Figure 6B:
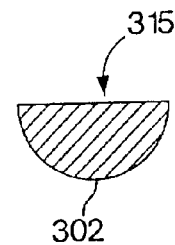
Figure 8:
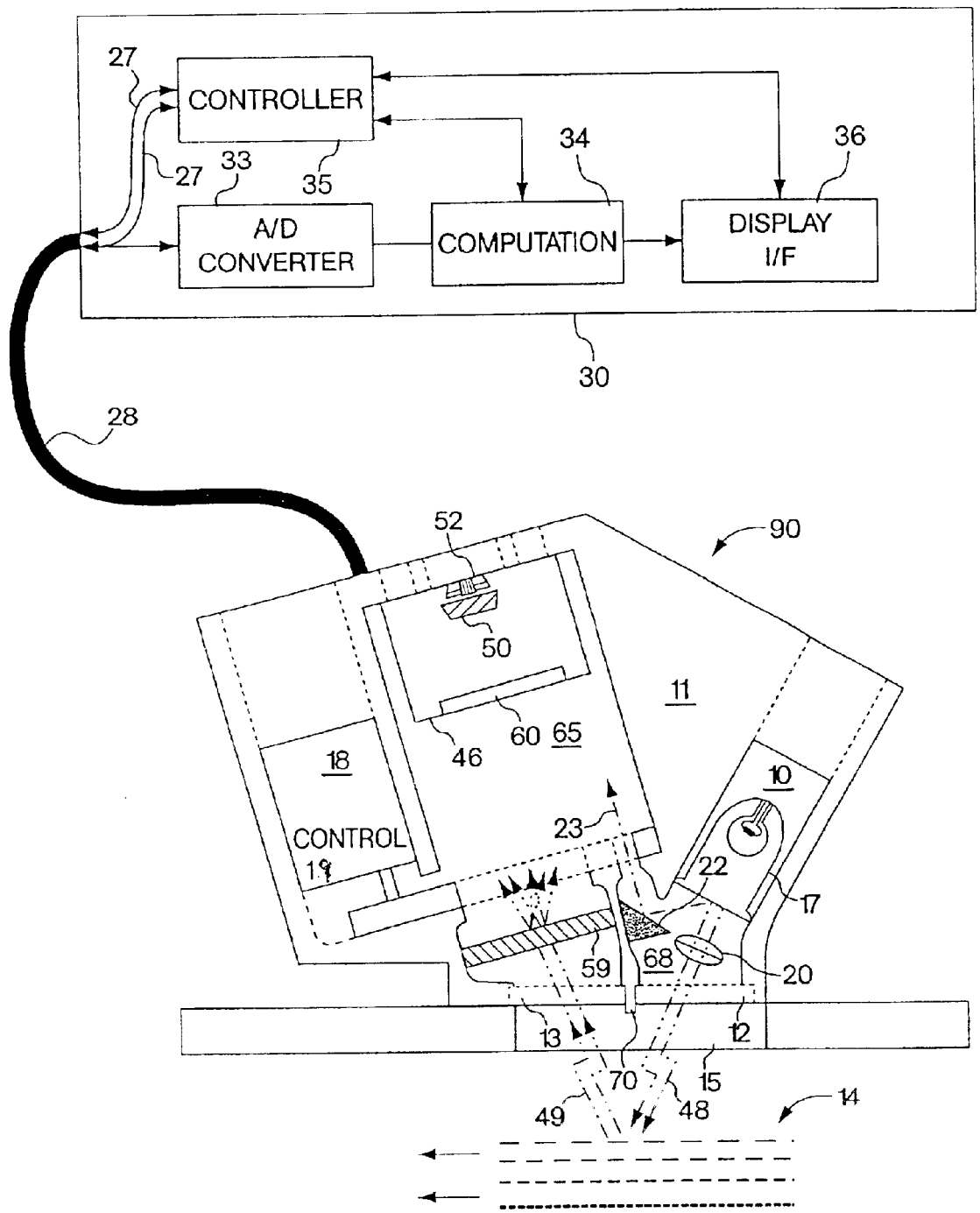
FIG. 8 is a schematic illustration of a spectral analyzer, according to the present invention.

FIGS. 6a and 6b illustrate an exemplary embodiment according to the present invention that is capable of being variably positioned in contact with the moving surface of a flowing material 350. The illustrated probe 300 includes a probe head 301 having a light source 304 arranged to irradiate a sample volume 310 of the flowable material 350, such as grain, as the grain passes an irradiation window proximate the probe head 301. The light source 304 may be a lamp or other radiation source disposed in the probe head 301, or it may be the radiant end of an optical fiber or other waveguide delivering light from a source distal to the probe head 301. The probe head 301 may also include an optical pick-up 306, arranged to receive light emitted from the sample in the irradiated sample volume 310 and transmit the received light to, for example, a spectrometer, for analysis. The probe head 301 can be configured as illustrated in FIG. 8, discussed in detail below. Alternatively, the probe head 301 can be configured in a manner analogous to the probes described in commonly owned U.S. Pat. No. 6,100,526, incorporated herein by reference, or in other manners known in the art.

Figure 6C:
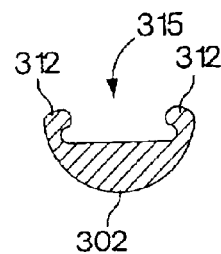

As the illustrated probe 300 is designed to be in contact with the surface of the flowing material 350. The probe preferably includes a planing element 315, that preferably is planar in shape and has a contact surface 302. The contact surface 302 is shaped in a convex downward fashion, as illustrated in FIG. 6a, such that when the planing element contacts the surface of the moving material 350, the planing element 315, and, thus, the probe 300, skims the surface of the flowing material 350 without creating significant turbulence in the material. Preferably, the planing element 315 is oriented at an angle of attack 316 that is relatively shallow, for example, less than 15°, to further minimize turbulence in the sample material. One skilled in the art will appreciate that the shape and curvature of the contact surface 302 of the planing element 315 can be optimized for the material being probed and is not necessarily limited to the convex shape described herein. For example, the planing element 315 can optionally have a curved lip 312 along its periphery to further minimize turbulence in the material, as illustrated in FIG. 6c.

The planing element 315 can be made from such materials as stainless steel, steel or aluminum; or made from moldable and durable plastic; or from other materials. The material of the planing element 315 is preferably optimized to the material being analyzed. For example, the planing element 315 can be made from a strong, abrasive resistant metal, ceramic, or other material to facilitate measurement of an abrasive material such as grain. Alternatively, the planing element can be made from a low-friction material or coated with a friction reducing material.

The illustrated probe 300 is supported by a shaft 318 and may also include a constant force generator 320 for applying a constant static force to the planing element 315 of the probe head 301 to maintain the planing element 315 in contact with the surface of the sample 350. The constant force generator 320 can be a spring, weight or pneumatic system such as a piston device for tensioning the probe head 301 against the sample 350. The exemplified probe 300 may also be provided with bearings 325 to help guide the motion of the shaft 318 supporting the probe head 301.

Figure 7A:
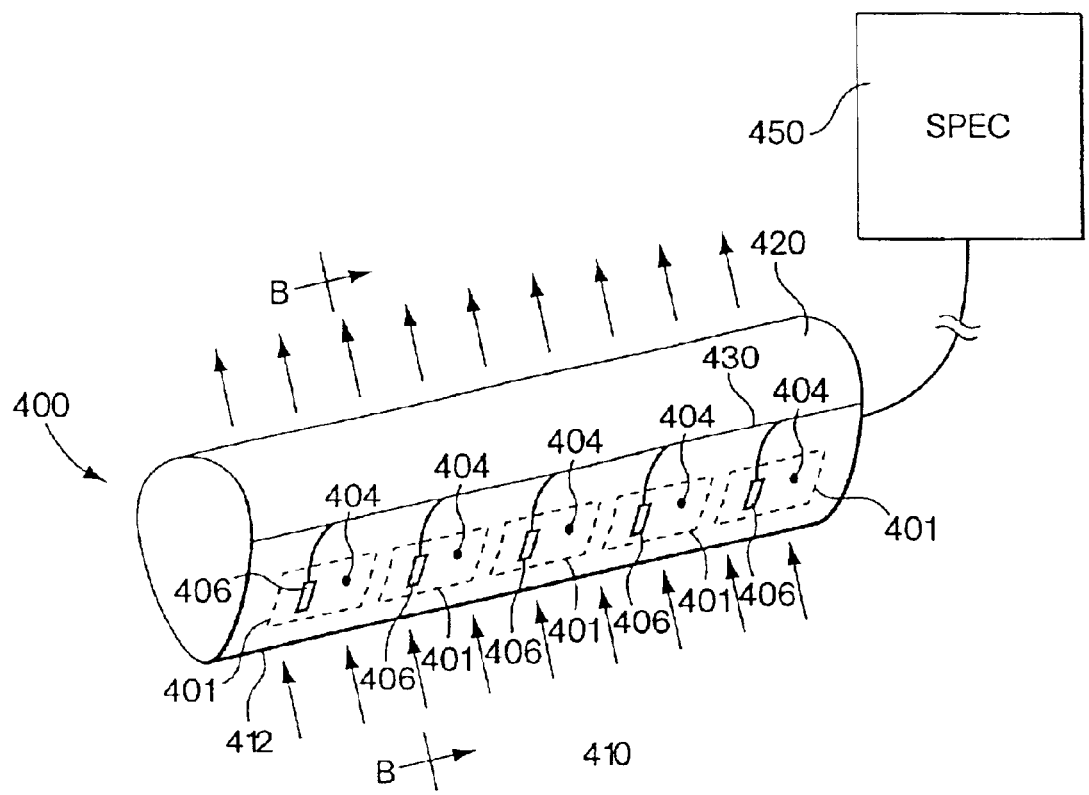
FIG. 7a is a schematic drawing of a multiple probe head apparatus for analyzing a stream of flowable material, according to the present invention.

FIG. 7a illustrates yet another aspect of the present invention, showing an embodiment of a multihead probe system for spectroscopic analysis of a moving sample of a flowable material. In particular, the invention provides a probe assembly 400 including a plurality of probe heads 401, e.g., which are simultaneously (relative to each other) able to irradiate and collect spectral information on a moving sample 410. The probe heads 401, in the illustrated embodiment, are disposed in a common housing 420 which is preferably shaped so as to minimize turbulence in the moving sample 410. Preferably, the housing 420 is streamlined in shape, with the shape providing a large force normal to the free stream of the material and as little drag as possible. In one embodiment, illustrated in FIG. 7b, for example, the housing 420 may be shaped like an airfoil, having a rounded leading edge 412 that prevents flow separation.

In general, each of the plurality of probe heads 401 may include a light source 404 arranged to irradiate the moving sample 410. The light source 404 may be a lamp or other radiation source disposed in the probe head 401 or it may be the radiant end of an optical fiber or other waveguide (not shown) delivering light from a source distal to each of the probe head 401.

The probe heads 401 will also each include an optical pick-up 406, arranged to receive light energy reflected or otherwise emitted from a sample in the irradiated sample volume. The optical pick-up 406 receives light reflected or emitted from a moving sample 410 being irradiated, and is in optical communication with one or more detectors of the spectrometer which measure the intensity of the reflected light, e.g., in a wavelength-dependent manner. The detectors can be located distal to the probe head 401 in a spectrometer 450, as illustrated in FIG. 7a, and the optical pick-ups 404 may each be an aperture in the probe head 401 connected with an optical fiber 430 or other waveguide which communicates light reflected or emitted by the moving sample 410 to the detector. Alternatively, the detector may be proximal to the irradiated sample, e.g. with the probe head 401, and the pick-up may simply be an aperture for permitting light being reflected by the sample to enter the probe head. Such a probe head is illustrated in FIG. 8 and described in more detail below.

Figure 7B:
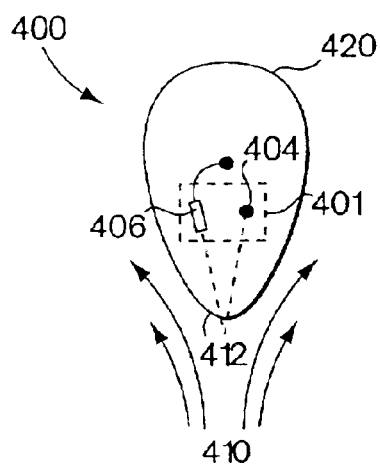

In certain embodiments, the probe heads 401 can be arranged along the longitudinal axis of the shaft, such as shown in FIG. 7a. In other embodiments, the probe heads 401 may be arranged in a two dimensional matrix. There may be from as few as 2 probe heads 401 to, in certain embodiments, hundreds of probe heads 401 in the array. The probe heads 401 can be placed below the center line of the housing 420, as illustrated in FIGS. 7a and 7b, or can be located in other positions within the housing. Preferably, the probe heads 401 are located along common axes that are preferably oriented parallel to the longitudinal axis. The probe heads 401 may be evenly spaced along each axis, as illustrated, or may alternatively be placed at independent, discreet distances from one another depending on the shape of the housing 420 and the material being analyzed.

Each probe head 401 may include a single light source and a single optical pick-up, as illustrated in FIGS. 7a and 7b. This would facilitate, for example, probe heads 401 placed so as to sample the flowing material from two different locations. Alternatively, the housing 420 may include more probe heads than light sources, so that one light source provides light for more than one probe head 401. This would facilitate, for example, multiple measurements made simultaneously increasing the temporal utilization of a spectrometer. A skilled artisan recognizes that these simultaneous measurements are averaged in a rigorous way which maximizes resolution.

Likewise, the multiprobe head systems can include fewer spectrometers or detectors than probe heads 401, wherein the signals from multiple pick-ups are combined before being communicated to the detector. Alternatively, the spectrometers can be set for series or parallel multiplexing of the optical signals in the pick-ups.

FIG. 8 shows a probe head 90 for analyzing the constituent or color components of a sample 14. The applications of the spectral analyzer device are rather unlimited as it can be used in any situation that requires or benefits from a large illumination spot size and wide angle viewing detector. The probe head 90 is particularly suited for use in the embodiments described above in connection with FIGS. 6a–c and 7a–b.

The probe head 90 uses a suitable continuous or pulsed irradiating light source 10. Radiation from the light source 10 shines forward through a first window 12 to the surface of a sample 14. The light source 10 simultaneously produces light of multiple wavelengths in a region of interest. Depending on the application, the present invention supports wavelength analysis in a range of UW, visible, and infrared nanometers. The actual range of light used in a particular application depends on the wavelength response of the detector which is matched with a light source capable of emitting such wavelengths.

The desired range of wavelengths to be analyzed dictates the type of detector used in the present invention, which typically is wavelength limited. For example, a fairly inexpensive silicon photodiode array is capable of detecting light intensities of wavelengths between 400 and 1100 nanometers. Other detectors optionally used in the invention are lead sulfide and lead selenide detectors, which support a response between 1000 to 3000 nanometers and 3000 to 5000 nanometers respectively. Optionally, other detectors used in the invention for near-infrared radiation include silicon, germanium, InGaAs, and PMTs (Photo-Multiplier Tubes).

The light source 10 is positioned to shine upon the sample 14 to be analyzed. Preferably, the light source 10 is a quartz halogen or tungsten filament bulb and is widely available.

The light source 10 and related components are preferably positioned within a suitable housing 11. In such an instance, a first window 12 is disposed between the light source 10 and the sample 14 to be analyzed. This prevents debris from entering the cavity and obstructing the illuminating light source 10. The first window 12 is formed of a suitable material, such as sapphire or glass, which is transmissive at the wavelengths of interest, and which does not see a significant absorption shift due to temperature changes. Sapphire also resists scratching and, therefore, debris brushing against its surface will not damage the window.

The housing 11, including the enclosed light source 10, first window 12, and other related components to be described, is thus positioned to monitor the sample 14 to be analyzed. This is accomplished by positioning the housing 11 such that light radiating from the light source 10, shines through the first window 12 onto the sample 14.

The housing 11 can be positioned such that the first window 12, as well a second window 13, contact an observation window 15, which may be a part of a preexisting window in a sample containment apparatus, e.g. an observation window in a vat, bin, or the like.

A parabolic mirror or reflector 17 is disposed within the light source cavity to direct light from the light source 10 to the sample 14 being analyzed. In the preferred embodiment, the light emanating from light source 10 is either collimated or focused to enhance the intensity of the light reflected off the sample. However, lens 20 optionally provides a means of additionally focusing or de-focusing the light into a more or less intense beam. In other words, the irradiated light shining on the sample 14 is optionally focused to enhance the source.

In an alternate embodiment, more than one light source 10 can be used, such as an array of e.g., semiconductor lasers or light emitting diodes. Typically, the array would be focused on the same point.

It is preferred that the light source 10 be placed such that it directly illuminates the sample 14 to be analyzed through the first window 12 with no fiber optic or other device other than the first window 12 itself being disposed between the light source 10 and the sample 14.

In the preferred embodiment, the illumination spot size from the light source 10 onto the sample 14 is approximately 1 to 3 inches in diameter, creating a spot of light between 0.5 and 10 square inches. Effectively, the incident light 48 shines through the first window 12 onto the sample 14 to produce reflected light 49 directed towards the second window 13 and an analysis chamber where light intensities are analyzed.

A wide illumination spot size and corresponding viewing aperture is preferred because it results in more accurate measurements of the sample 14 to be analyzed. This is due to the fact that small inhomogeneities relative to the larger spot size within a sample region are typically negligible with respect to the whole. In other words, the wider spot size produces a better averaging effect because a potential inhomogeneity in a sample is not at the focus of the illumination spot.

Without a wide viewing aperture, colorimeter and constituent measurements based on small spot sizes can produce inaccurate results if the operator of such a device erroneously takes a sample measurement of an inhomogeneity in the sample not representative of the whole. For example, a small black spot on a dark blue background barely detectable by the naked eye could fool an operator that the color of the sample is black rather than blue. The above-described probe embodiments help to reduce erroneous colorimeter measurements by advantageously including a wider illumination spot size and viewing detector to support the aforementioned color averaging effect.

Spectral analyzers available in the market often incorporate costly optical hardware for receiving the light reflected off a sample 49 and directing it to an optical detector located at a distance. To view even a small spot with these systems requires a high intensity light source. This method of using optical hardware to redirect the reflected sample light 49 limits the spot size to a narrow diameter because the reflected light must be focused into a small fiber optic cable.

The exemplary embodiment described, on the other hand, advantageously positions a detector 52 with a wide viewing aperture located in a second chamber 65 immediately adjacent the first chamber 68 to receive the reflected sample light 49. This eliminates the need for costly fiber optic hardware because received light no longer needs to be directed to a detector at a remote location. Rather, reflected sample light 49 naturally strikes a detector 52 located immediately in the second chamber 65. To match the performance of the present probes, a fiber system would require a very large fiber bundle for redirecting reflected sample light to a remote detector.

An optical blocking element 70 also serves to separate the first and second windows 12 and 13 and to force the optical path of the light source 10 and the detector 52 into the sample 14. In this manner the incident light 48 and the sample light 49 intersect within the sample 14 and thereby discriminate against (prevent) direct surface reflection by inhibiting light directly reflected from the first window 12 and from the surface of the sample at the window 12 from reaching the detector 52.

Eliminating the fiber optic pickup and associated fiber optic cables has advantages in addition to enabling the use of a wider illumination spot size. Typically, fiber optic cables have a limited transmission bandwidth. Hence, when they are used to steer reflected light to a detector located far away, the spectral range of directed light is limited to the transmission bandwidth of the cable. Moreover, the use of fiber optic cables are further prohibitive because the fiber optic cables supporting the wavelengths of mid infrared are particularly expensive and have large throughput losses associated with them. In some cases, just a few meters of this type of cable can be more than a thousand dollars. The exemplary probe head 90 illustrated in FIG. 8 is not as bandwidth limited nor burdened with unnecessary additional cost because it does not incorporate any fiber optic cables to transmit light.

The use of a fiber optic cable to transmit the reflected sample light 49 is additionally undesirable because the integrity of the optical signal within a fiber optic cable is susceptible to heat distortion and mechanical vibrations. This is especially true when the fiber optic cable supports the transmission of light in the infrared region. Both the heat distortion and mechanical vibrations, particularly prevalent in a portable device, negatively impact the integrity of the mode structure of the optical signal used to detect constituents in a sample. By placing the detector 52 in a second chamber 65 immediately adjacent the light source 10 without incorporating an optical fiber in the reflected sample light path 49, the probe head 90 advantageously avoids the aforementioned problems.

The probe described above replaces the small fiber, which typically has an aperture area of less than 1 square millimeter, with a large viewing aperture of typically 0.5 to 10 square inches. This allows for viewing large fields of view with low light intensities. With additional optics, the aperture size can be adjusted to create a variable field of view and allows a large sample to be imaged from a distance.

As mentioned, light emitted by the light source 10 passes through the first window 12 into the sample 14 to be analyzed. Incident light 48 from light source 10 then reflects off the sample 14, where the reflected sample light 49 is angularly directed back through second window 13.

In the preferred embodiment, the angle of the light source 10 and detector unit 52 in the second chamber 65 are optimized so that most of the reflected sample light 49 is directed to the second chamber 65 for spectral analysis of the sample 14. For example, the light source 10 may be optimally angled at approximately 60° relative to the first window 12 while the detector unit 52 in the second chamber 65 may be angled at approximately 60° relative to the second window, as shown in illustrative FIG. 8.

The first and second window 12, 13 are preferably parallel and in the same plane as shown. However, other embodiments optionally include windows that are positioned at an angle with respect to each other, while the first and second chamber 65, 68 are still positioned adjacent to each other.

The second chamber 65, as mentioned, includes optical devices for detecting the reflected sample light 49. Specifically, the reflected sample light 49 passes through the second window 13 into the second chamber 65 where it is spectrally analyzed. Diffuser 59 acts to scatter the reflected sample light 49, spatially distributing the intensity of the light throughout the second chamber 65 for more accurate simultaneous spectral readings and to prevent imaging of the sample. For example, reflected sample light 49 of various wavelengths is more evenly distributed throughout the second chamber 65. Otherwise, high intensity light regions caused by reflected sample light 49 results in less accurate constituent measurements due to imaging effects.

Hermetically sealed chamber 46 is positioned in the second chamber 65 to receive reflected sample light 49. An optically transmissive third window 60 allows diffused light emanating from the diffuser to shine onto wavelength separator 50 and array detector 52 (e.g., CCD), both of which are positioned within the hermetically sealed chamber 46. This airtight chamber protects sensitive optical components from corrosive and measurement-inhibiting elements such as humidity and dust. Without the hermetically sealed chamber 46, a buildup of dust and other debris on the detection unit 52 and wavelength separator 50 will negatively effect constituent measurements. It should be noted that all, none or part of the second chamber 65 is optionally designed to be hermetically sealed.

The wavelength separator 50 within hermetically sealed chamber 46 in a preferred embodiment provides spatial separation of the various wavelengths of diffusely reflected light energy of interest. Suitable wavelength separators 50 include linearly variable filters (LVF), gratings, prisms, interferometers or similar devices. The wavelength separator 50 is preferably implemented as a linearly variable filter (LVF) having a resolution ($\Delta\lambda/\lambda$, where X is the wavelength) of approximately one to four percent.

The now spatially separated wavelengths in turn are fed to the detector 52. The detector 52 is positioned such that it simultaneously measures the response at a broad range of wavelengths. In the preferred embodiment, the detector 52 is an array of charge coupled devices (CCDs), which individually measure the light intensity at each of the respective wavelengths. In other words, each cell of the CCD array is tuned to measure the intensity of an individual bandpass of light.

Other suitable detectors 52, however, are constructed from fast scan photodiodes, charge injection devices (CIDs), or any other arrays of detectors suitable for the task of simultaneously detecting the wavelengths of interest.

In a preferred embodiment, the detector 52 is a silicon CCD array, such as a Fairchild CCD 133A available from Loral-Fairchild. This CCD array 52 is a 1,024-element array processing wavelengths in the range from about 570 to about 1120 nm. As mentioned, other detectors supporting different bandwidths are optionally used.

In addition, the detector 52 such as a CCD array is typically temperature sensitive so that stabilization is usually preferred. Cooling is achieved using a thermoelectric cooler.

The preferred embodiment of the present probe also includes a reflector 22 disposed in the first chamber to reflect reference photons 23 to the wavelength separator 50 and detector 52 positioned in the second chamber 65 depending on the position of the light blocking shutter, discussed below. The reflector 22 is preferably fixed such that repeated measurements are based upon the same reference light intensity.

A light blocking shutter 19 is provided to selectively allow the appropriate light to flow into the second chamber 65. Shutter 19 controls the passage of either sample light 49 into the second chamber 65, or the passage of reference light 23 reflected off reference light reflector 22 into the second chamber 65. The second shutter 19 can also be used to block all incoming light for measuring a "dark" reference signal. Shutter 19 can also be implemented as a dual shutter mechanism, as will be understood by one of skill in the art.

Control electronics and shutter motor 18 located adjacent to the second chamber 65, provide a mechanism for controlling light into second chamber 65. Shutter position commands are received via electronic signals transmitted by controller 35 residing in the electronics block 30.

Light blocking shutter 19 is appropriately positioned for each of three measurements. A first measurement involves blocking both the reflected sample light 49 and reference photons 23. This reference measurement of the "dark" second chamber 65 serves as a means of calibrating the detector unit or array 52. A second measurement involves blocking the reflected sample light 49 and measuring the reference photons 23. This measurement serves to calibrate the system to the light source 10. Finally, a third measurement involves blocking the reference rays 23 and measuring the reflected sample photons 49. Details of the measurements and related computations are further described in FIG. 9.

The electronic signals 27 are bundled together in a wire harness 28 connecting the probe head housing 11 and electronics block 30. In a practical deployment of the probe head 90, it is preferred that the electronics block 30 be as close. as possible to housing 11. However, in some applications it may be necessary to separate the probe head 90 and electronics block 30.

The electronics block 30 includes an analog to digital converter 33, a constituent computation function 34, a controller 35, and a display interface 36. In the preferred embodiment, the computation function 34, controller 35 and display interface 36 are implemented as software in a computer, microcontroller, microprocessor and/or digital signal processor. Electronic signals 27 in wire harness 28 provide connectivity between the electronics in the probe head housing 11 and the electronics block 30.

As mentioned, one application of the systems of the present invention involves mounting the electronics block 30 in a shielded environment, such as a cab, while the probe head 90 is mounted in a position to detect the sample 14 to be analyzed. Therefore, based on this separation, the electronics are designed to ensure that signal integrity does not suffer because of the length of the wire harness 28. For example, the electronic signals 27 within wire harness 28 are properly shielded to prevent excess coupling noise, which may deleteriously effect A/D readings of the CCD array detector 52. The controller 35 coordinating the A/D sampling process, as mentioned, controls the shutter mechanisms positioned in the second chamber 65 for the various spectral measurements.

The individual electrical signals provided by the CCD for each wavelength are then fed from the output of the detector 52 to analog to digital converter 33 where the electrical signals are converted to digital signals for processing.

A computation block 34, preferably implemented in a microcomputer or digital signal processor as described above, then carries out calculations on the basis of the received wavelength intensities to obtain either the color characteristics or percentage concentrations of constituents of the sample 14. The results of the sample analysis are then communicated to an operator in any desired way such as by a meter or presenting them to a display. The display is optionally integral to a laptop computer or display, such as an LCD, on or near the electronics block 30 or probe head 90. The computation block may be part of the electronics block 30 or may be physically separated from it.

In the preferred embodiment, the electronics block 30 and probe head 90 are integrated to produce a handheld portable spectral analyzer. This embodiment is particularly beneficial in colorimeter applications that require analyzing the sample in a fixed location such as a home where, for example, wallpaper or paint is fixed to a wall. Based on its portability, the analyzer is easily maneuvered to test samples in awkwardly tight spaces. Additionally, because of its small size, it is less likely to be damaged or dropped during transit or use.

The analyzer may also support calculating constituent concentrations in samples such as grain. Techniques for calculating percentage concentrations of grain based upon samples of light and particular wavelengths are the multivariate techniques detailed in the book by Sharaf, M. A., Illman, D. L., and Kowalski, B. R., entitled "Chemometrics" (New York: J. Wiley Sons, 1986).

Preferred wavelengths of interest depend upon the constituents being measured. For example, when measuring protein concentration, the algorithms makes use of absorptance attributable to the vibration-rotational overtone bands of the sub-structure of protein. At longer wavelengths absorption coefficients are large, the path length is short, and thus one would not sample the interior of the grain particles. At shorter wavelengths the absorption coefficients are small and the signal is thus weak.

The probe head 90 provides for irradiation of the sample followed by spatial separation and detection of multiple wavelengths in parallel, making for rapid analysis of this sample. Moreover, since the optical portions of the unit are substantially insensitive to vibrations, the probe head 90 may be deployed in environments where real time analysis of samples is performed in harsh environments.

Furthermore, the use of the CCD array as detector unit 52 provides advantages over prior art techniques that use discrete or scanned diode arrays. In particular, the CCD bins are all filled with charge at the same time. in parallel with one another. They are then emptied and the results read out by the controller 35 are processed while the CCD array begins filling again. Based on sampling over a time period, each pixel or bin detects reflected light intensities off the sample over the same time interval. This is particularly important if the sample happens to be moving across the viewing region of the device. In contrast, diode arrays must be read sequentially so that for example, any given element is producing a signal from the sample that is distinct from those seen by previous pixels.

The signal to noise ratio of the probe head 90 measurements may be improved by averaging over the course of many measurements.

Figure 9:
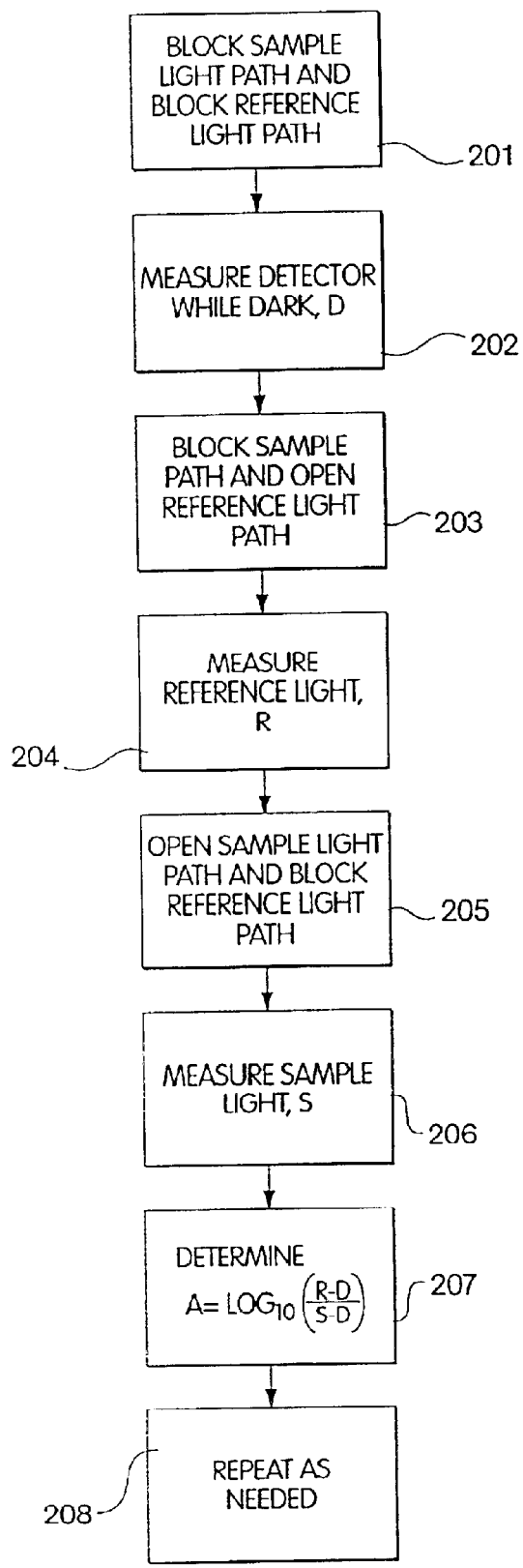
FIG. 9 is a flow chart depicting a process for measuring absorptivity of a sample according to the principles of the present invention.

The preferred absorption measurement includes the following process illustrated in FIG. 9:

1. Block both the sample reflection light and reference light from the wavelength detector unit (step 201)
2. Perform a reading on the wavelength detector unit, storing measurement data in D for dark spectrum (step 202).
3. Block the sample reflection light and allow reference light to shine on wavelength detector unit (step 203).
4. Perform a reading on the wavelength detector unit, storing measurement data in R for reference light spectrum (step 204).
5. Block the reference light and allow sample reflection light to shine on wavelength detector unit (step 205)
6. Perform a reading on the wavelength detector unit, storing measurement data in S for sample spectrum (step 206).
7. Calculate the absorptance spectrum A, where the light absorption as derived from these diffuse reflectance measurements is given by:

$$A = LOG_{10}(R-D)/S-D).$$

Further data processing therefore may provide a second derivative of absorptance spectrum A to remove constant and linear offsets so that only quadratic and higher order features in the absorptivity spectrum are utilized in the determination of protein content. In addition, since the absorptivity variations from the presence of protein are quite small, multiple realizations, averaging, and second derivative analysis are typically used to produce the desired absorptivity number at a particular wavelength.

Figure 10A:
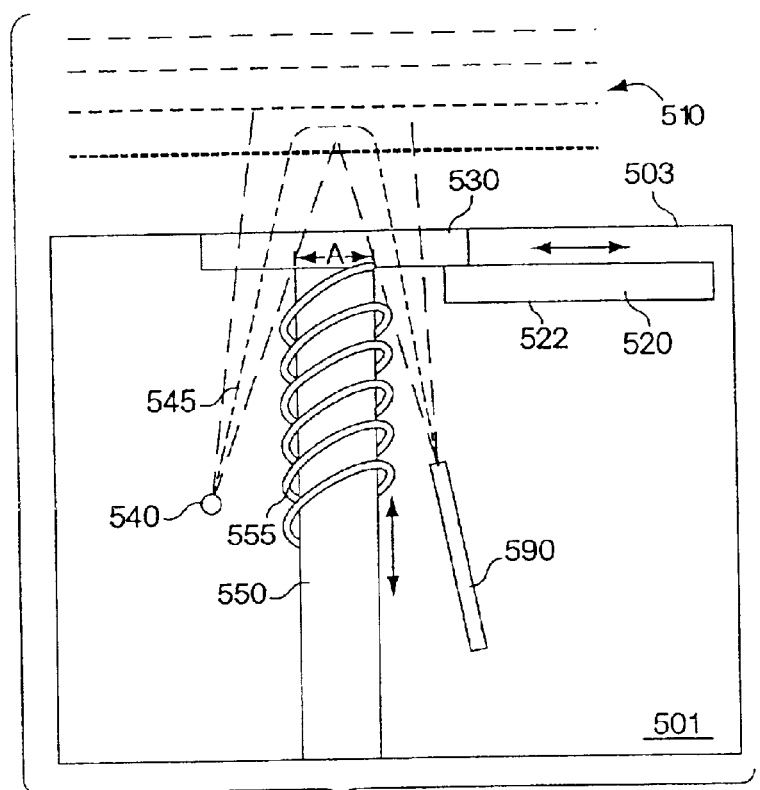
FIGS. 10a and 10b are schematic illustrations of an alternative embodiment of an optical probe head of the present invention.
Figure 10B:
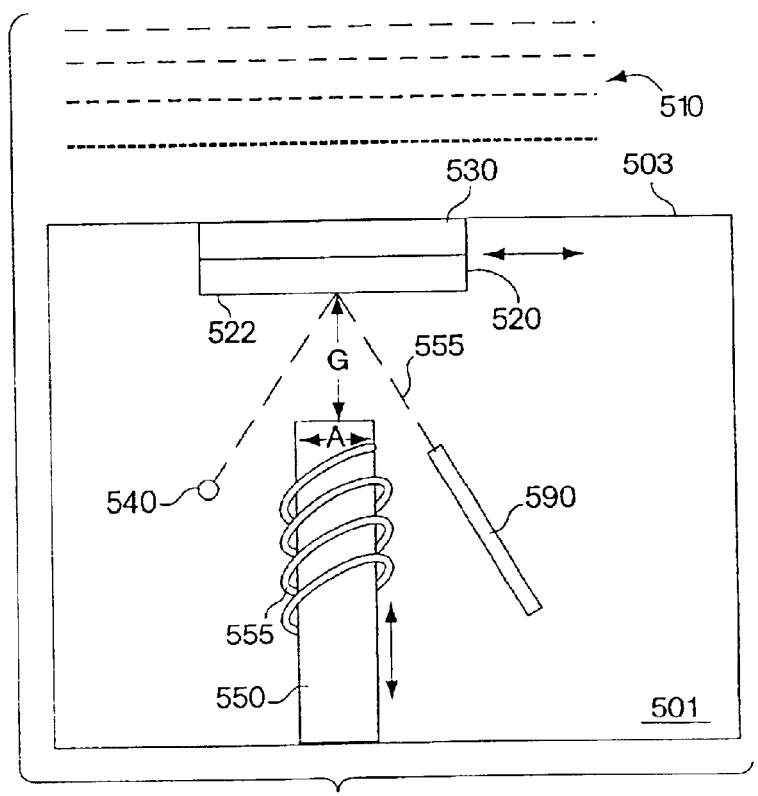

An alternative embodiment of a probe head for use with a spectrometer to analyze material is illustrated in FIGS. 10a and 10b. The probe head 501 is particularly useful for analyzing materials having diffuse reflecting properties such as powders, slurries, etc. The probe head 501 includes a light source 540 for irradiating a sample volume of the material 510 proximate the probe head 501 through a window 530 formed in the probe head 501. The light source 540 may be a lamp or other radiation source disposed in the probe head 501, or it may be the radiant end of an optical fiber or other waveguide delivering light from a source distal to the probe head 501. Alternatively, more than one light source 540 may be used, such as an array of e.g. semiconductor lasers or light emitting diodes. Preferably, the array would be focused on the same point. The window 530 may be formed of a suitable material, such as sapphire or glass, which is transmissive at the wavelengths of interest, and which does not allow for a significant absorption shift due to temperature changes.

The probe head 501 may also include an optical pick-up, such as, for example an optical fiber 590, arranged to receive light emitted from the sample in the irradiated sample volume and transmit the received light to, for example, a spectrometer, for analysis. The optical fiber 590 may be a single fiber or a multiple fiber bundle capable of both incoherent and coherent waves. The optical fiber 590 may be made from quartz, glass, plastic or other transmitting materials. Preferably, the optical fiber 590 has a numerical aperture of 0.2 to 0.5. Optionally, the optical fiber 590 can be hollow, with adequately reflecting walls. Alternatively, the optical fiber 590 may be replaced in situ by a detection system, such as, for example, in the manner of the probe head described above in connection with FIG. 8.

The probe head 501 may be constructed out of metals such as stainless steel, steel or aluminum; or made from moldable and durable plastic; or other materials. The materials may be translucent, transparent, or opaque and may be chosen for ease of cleaning and maintenance. The probe head 501 can also be constructed of material which optimizes the appropriate measurements of the sample material. The exterior surface 503 of the probe head 501 may be geometrically shaped to optimize the probe measurements.

The exemplary probe head 501 may also include an optical blocking element 550 positioned in the optical path between the light source 540 and the light collecting optical fiber 590. The optical blocking element 550 forces the path of light into the material 510 thereby reducing error due to surface reflection and increasing the signal to noise ratio of the spectral analysis. The optical blocking element 550 is opaque and preferably is in contact with or effectively splits/bifurcates the window 530. The optical blocking element 550 may be constructed out of metals such as stainless steel, steel or aluminum; or made from moldable and durable plastic; or other opaque materials. In one preferred embodiment, the optical block element 550 is biased into contact with the window 530 by spring loading, via a spring 555 or by other biasing mechanisms.

A typical, theoretical light path 545 is shown in FIG. 10*a* to illustrate an optical path of light into and reflected from the material 510 during data collection. The optical block element 550 effectively minimizes the direct surface reflection from the window 530 or the material 510 by blocking such direct surface reflection from reaching the optical fiber 590. In this manner, the allowed optical paths, including theoretical optical path 545, originates from light source 540, undergoes diffusive transport in the material 510, and is collected and transported within the numerical aperture of the optical fiber 590.

The probe head 501 may include a reference shutter 520 for calibrating or re-normalizing the spectrometer, in particular the signal processing algorithm of the spectrometer, to account for any signal changes relative to previous calibrations of the spectrometer. The reference shutter 520 includes a reflective surface 522 having a reasonably uniform value of reflectance over the wavelength of interest. To be effective for calibration, the reflectance value of the reflective surface preferably remains unchanged with regards to time, temperature, usage, etc. The reflective surface 520 may be made out or, or coated by, stable reflective materials such as gold, white ceramics, Spectralon®, stable white paint, and other such materials.

The reference shutter 520 is movable between an open, measurement position, illustrated in FIG. 10*a*, and a closed, calibration position, illustrated in FIG. 10*b*. In the open, measurement position, the reference shutter 520 is positioned out of the optical path between the light source 540 and the optical fiber 590 to facilitate spectral analysis of the material 510. In the closed, calibration position, the reference shutter 520 is positioned in the optical path between the light source 540 and the optical fiber 590 to effectively block light from the sample material 510 from reaching the optical fiber 590. As shown in FIG. 10*b* by illustrative, theoretical optical path 555, light from the light source 540 reflects off the reflective surface 522 to the optical fiber 590. The reference shutter 520 may be moved between the closed and open positions by a rotary solenoid, or by other electromagnetic, electromechanical, or mechanical mechanisms.

During calibration of the system, it is preferable that the optical blocking element 550 be moved away from the window 520 to allow the reference shutter 520 to move into the closed position, as illustrated in FIG. 10*b*. Preferably, the optical blocking element 550 is moved a distance from the window 520, e.g., gap G in FIG. 10*b*, such that sufficient light from the light source 540 can reflect from the reflective surface 522 of the shutter 520 and reach the optical fiber 590 at an angle within the numerical aperture of the optical fiber 590. The optical blocking element 550 can be moved towards and away from the window 530 by a rotary solenoid, or by other electromagnetic, electromechanical, or mechanical mechanisms. Alternatively, the movement of the optical blocking element 550 can be mechanically coupled to the movement of the shutter 520, as discussed below, such that separate movement mechanisms, e.g. solenoids, for the optical blocking element 550 and the shutter 520 are not necessary.

Figure 11A:
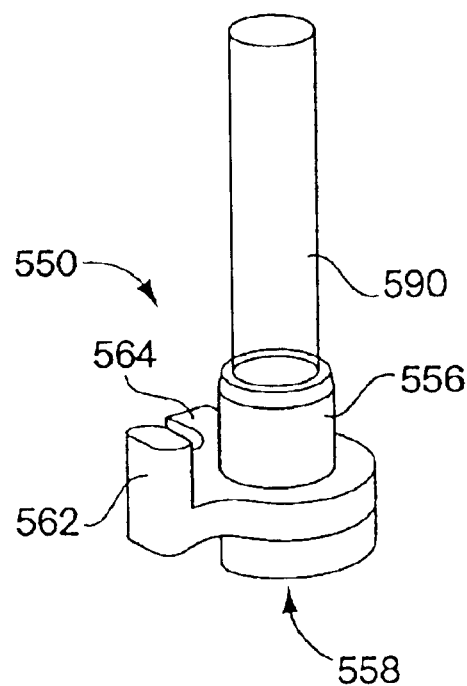
FIGS. 11a and 11b are perspective views of one embodiment of the optical blocking element of the probe head of FIGS. 10a and 10b.
Figure 11B:
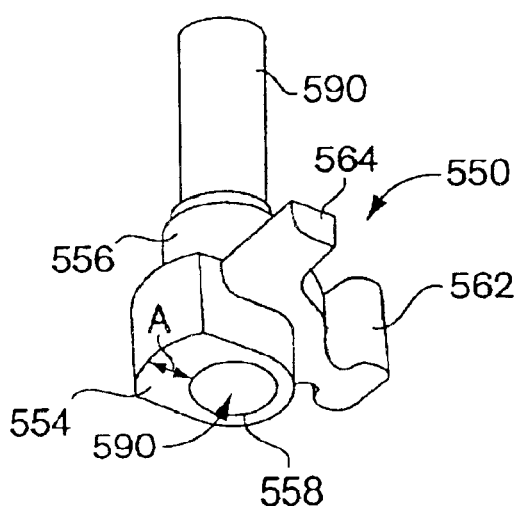
Figure 12:
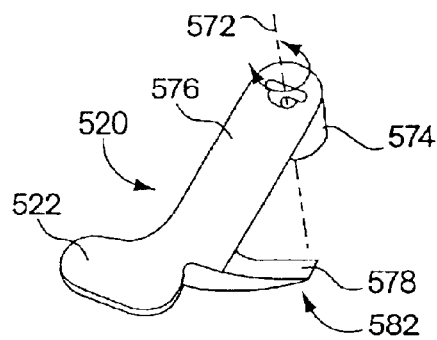
FIGS. 12a and 12b are perspective view of one embodiment of the reference shutter of the probe head of FIGS. 10a and 10b.
Figure 12:
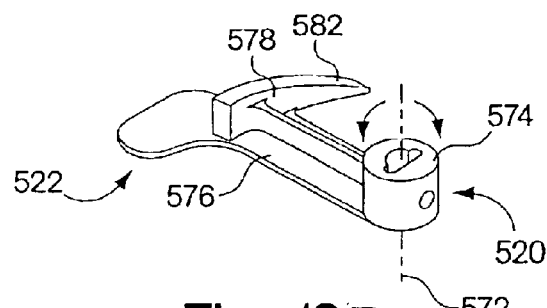
Figure 13:
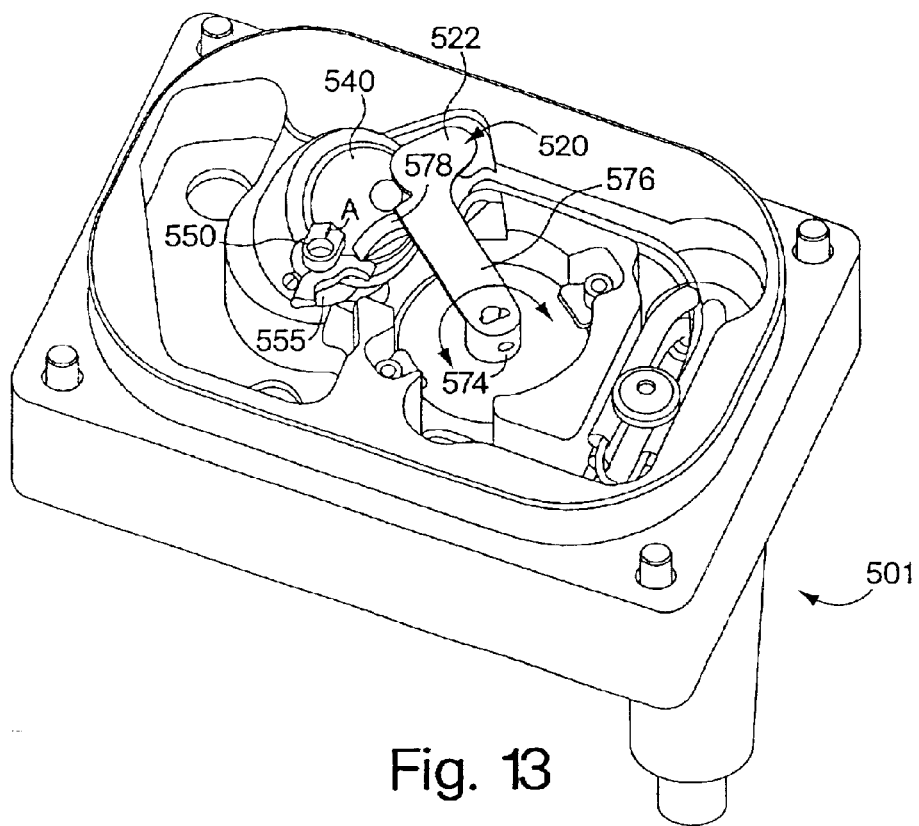
FIG. 13 is a perspective view of an optical probe head implementing the optical blocking element and the reference shutter of FIGS. 10a–b and 11a–b, respectively, illustrating the probe head of the optical window with the sample window removed.

FIGS. 11–13 illustrate an exemplary, preferred embodiment of the probe head 501. FIGS. 11*a* and 11*b*, illustrate a preferred embodiment of the optical blocking element 550. The exemplary optical blocking element 550 includes a blocking surface 554 for contacting the window 530 and a cylindrical housing 556 for attachment to the optical fiber 590. The cylindrical housing 556 includes an opening 558 for allowing light to enter the cylindrical housing and reach the optical fiber 590. Spring 555, as shown in FIG. 13, can be seated about the exterior of the housing 556 to bias the blocking surface 554 into contact with the window 530. The blocking surface 554 is sized and shaped to effectively block light directly reflected from the window 520 and the surface of the sample material 510. In particular, the width A of the blocking element, illustrated in FIG. 11*b*, is preferably optimized for the material 510 being probed and for the position of the light source 540 and the optical fiber 590 within the probe head 501, to minimize and, preferably completely block, light directly reflected from the window 530 and the surface of the material from reaching the optical fiber 590.

The optical blocking element 550 may include an arm 564 extending perpendicularly from the longitudinal axis of the housing 556, and thus, the optical fiber 590, and is provided to contact a camming surface of the shutter 520 to facilitate linear movement of the optical blocking element 550 when the reference shutter 520 is moved into the closed position, as discussed in more detail below. A second arm 562 may be included to be contained within a slot within the probe head 501 to prevent axial rotation of the optical blocking element 550.

An exemplary embodiment of the shutter 520 is illustrated in FIGS. 12*a* and 12*b*. The exemplary shutter 520 is configured for rotational movement about a rotation axis 572. The shutter 520 includes a cylindrical hub 574 that can be coupled to a rotary solenoid and an arm 576 that extends from the hub 574 in a direction perpendicular from the hub 574. The arm 576 is generally planar in shape and includes the reference surface 522 formed at the end distal from the hub 574. The reference surface 522 of the shutter 520 can thus be rotated about the rotation axis 572 between the open and closed position.

A camming arm 578 is provided proximate the reference surface 522 and extends generally perpendicular to the longitudinal axis of the arm 576. The camming arm 578 includes a camming surface 582 for engaging the arm 564 of the optical blocking element 550 in a camming relationship. As the shutter 520 rotates the reference surface 522 from the open position, illustrated in FIG. 10A, to the closed position, illustrated in FIG. 10*b*, the camming surface 582 engages the arm 564 of the optical blocking element 550 to move the blocking surface 554 out of contact with the window 530. Thus, the camming surface 582 translates the rotational motion of the shutter 520 into axial motion along an axis generally perpendicular to the window 530.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A probe head for use with a spectrometer to analyze a material, the probe head comprising:
   a light source arranged to irradiate a sample volume of the material proximate the probe head;
   an optical pick-up arranged to receive light emitted from the irradiated sample volume and transmit the emitted light to the spectrometer,
   a shaft having a longitudinal axis and housing the light source and the optical pick-up, and
   a reflector positioned within the shaft and having a first reflective surface for reflecting light from the light source through a wall of the shaft and into the sample volume to irradiate the sample volume, and having a second reflective surface for reflecting light emitted from the sample to the optical pick-up.

2. The probe head of claim 1, wherein the first reflective surface and the second reflective surface are each generally linear in shape.

3. The probe head of claim 1, wherein the first reflective surface and the second reflective surface are each generally elliptical in shape.

4. The probe head of claim 1, wherein the shaft includes:
   a first window formed in the walls of the shaft for transmitting light reflected from the first reflective surface into the sample volume, and
   a second window formed in the walls of the shaft for transmitting light emitted from the sample volume to the second reflective surface.

5. The probe head of claim 4, wherein the first window and the second window are generally annular in shape.

6. The probe head of claim 5, wherein the first window and the second window are each selectively transmissive about their circumferences.

7. The probe head of claim 1, wherein the first reflective surface is oriented to reflect at least a portion of the light from the light source in a direction generally perpendicular to the longitudinal axis of the shaft.

8. A probe head for use with a spectrometer to analyze a material, the probe head comprising:
   a shaft extending along a longitudinal axis;
   a light source arranged within the shaft;
   a reflector arranged within the shaft a longitudinal distance from the light source to reflect at least a portion of the light from the light source in a direction generally perpendicular to the longitudinal axis of the shaft to irradiate a sample volume of the material proximate the probe head; and
   an optical pick-up arranged within the shaft to receive light emitted from the irradiated sample volume and transmit the received light to the spectrometer.

9. The probe head of claim 8, wherein the reflector includes a passage for permitting light from the light source to be directly received by the optical pick-up.

10. The probe head of claim 9, wherein the passage is an optical fiber.

11. The probe head of claim 10, wherein the passage is an open tube formed in the reflector.

12. The probe head of claim 11, further comprising a first shutter for selectively blocking the passage.

13. The probe head of claim 8, further comprising an optical blocking element positioned in the optical path between the light source and the optical pick-up to force the optical path into the sample material.

14. The probe head of claim 8, further comprising a shutter for selectively blocking light emitted from the sample volume from reaching the optical pick-up to facilitate calibration of the spectrometer.

15. A method of spectroscopically analyzing a material comprising:
   inserting a probe head of a spectrometer into the material along an insertion axis, the probe head emitting light at least generally perpendicular to the insertion axis,
   moving the probe head along the insertion axis within the material to irradiate, with the probe head, a sample volume of the material, the sample volume extending at least partially about the circumference of the probe head, and
   analyzing light reflected from the sample volume of material.

16. A probe head for use with a spectrometer to analyze a flowing material, the probe head comprising:
   a light source arranged to irradiate a sample volume of the flowing material proximate the probe head;
   an optical pick-up arranged to receive light emitted from the irradiated sample volume; and
   a planing element shaped to cause the probe head to skim the surface of the flowing material when in contact with the flowing material.

17. The probe head of claim 16, wherein the planing element has a convex surface for contacting the flowing material.

18. The probe head of claim 17, further comprising a constant force generator for applying a constant force to the probe head to maintain the planing element in contact with the surface of the flowing material.

19. The probe head of claim 18, wherein the constant force generator is a spring, or a pneumatic element.

20. A probe assembly for use with a spectrometer to analyze a flowing material, the probe head comprising:
   a housing, having arranged therein, two or more probe heads for use with a spectrometer, wherein each of the probe heads are simultaneously able to irradiate and collect spectral information on the flowing material, and include
   (a) a light source arranged to irradiate a sample volume of the flowing material proximate the probe head, and
   (b) an optical pick-up arranged to receive light emitted from the irradiated sample volume;
   wherein the housing is shaped for disposal of the probe assembly in the path of the flowing material.

21. The probe assembly of claim 20, wherein the housing is aerodynamically shaped to minimize turbulence of the flowing material within the sample volume.

22. The probe assembly of claim 21, wherein the housing is shaped like an air foil having a leading edge, the leading edge being oriented to face the flowing material.

23. The probe assembly of claim 20, wherein the probe heads are arranged along a common axis within the housing.

24. The probe assembly of claim 20, wherein the probe heads are arranged along two or more common axes to create a two-dimensional array of probe heads.

25. The probe assembly of claim 20, wherein each optical pick-up is connected by way of a common optical fiber element to the spectrometer.

* * * * *